United States Patent
Hill et al.

(10) Patent No.: US 10,828,178 B2
(45) Date of Patent: Nov. 10, 2020

(54) METHODS AND APPARATUSES FOR FITTING AN OBJECT

(71) Applicant: BETHCARE, INC., Woburn, MA (US)

(72) Inventors: Jason Hill, Cambridge, MA (US); Elizabeth Tsai, Spring, TX (US); Ramin Abrishamian, Needham, MA (US); Jeremy Jo, Somerville, MA (US)

(73) Assignee: BETHCARE INC., Woburn, MA (US)

( * ) Notice: Subject to any disclaimer, the term of this patent is extended or adjusted under 35 U.S.C. 154(b) by 791 days.

(21) Appl. No.: 15/360,366

(22) PCT Filed: Jan. 22, 2015

(86) PCT No.: PCT/US2015/012452
§ 371 (c)(1),
(2) Date: Feb. 6, 2018

(87) PCT Pub. No.: WO2015/112712
PCT Pub. Date: Jul. 30, 2015

(65) Prior Publication Data
US 2017/0216056 A1    Aug. 3, 2017

Related U.S. Application Data

(60) Provisional application No. 61/930,304, filed on Jan. 22, 2014.

(51) Int. Cl.
*A61F 2/78* (2006.01)
*A43B 23/07* (2006.01)
*A41D 27/06* (2006.01)
*A61F 2/50* (2006.01)

(52) U.S. Cl.
CPC ............ *A61F 2/7812* (2013.01); *A41D 27/06* (2013.01); *A43B 23/07* (2013.01); *A61F 2002/503* (2013.01); *A61F 2002/5013* (2013.01); *A61F 2002/7818* (2013.01); *A61F 2002/7837* (2013.01); *A61F 2250/0003* (2013.01)

(58) Field of Classification Search
CPC .................. A61F 2/7812; A61F 2/7843; A61F 2002/7818; A61F 2002/785; A61F 2002/5013
See application file for complete search history.

(56) References Cited

U.S. PATENT DOCUMENTS

| | | | |
|---|---|---|---|
| 5,549,709 A * | 8/1996 | Caspers | A61F 2/5046 623/24 |
| 6,607,479 B1 | 8/2003 | Kochamba | |
| 2005/0137513 A1 * | 6/2005 | Rugfelt | A61F 5/05833 602/41 |

\* cited by examiner

*Primary Examiner* — David H Willse
(74) *Attorney, Agent, or Firm* — Boris Leschinsky

(57) ABSTRACT

Linings for fitting an object to a body part, and their use, are provided. The lining may include a flexible sheet having a fluid impenetrable outer portion enclosing an internal volume and the lining may include barriers forming a number of compartments substantially secured in place within the internal volume. The barriers may be permeable to gas and/or liquid, yet may be impermeable to the conformable material and the gas and/or liquid may be supplied to or aspirated from one or more compartments within the internal volume. Aspiration of gas and/or liquid from the internal volume may limit both deformation of the conformable material and shape adjustment of the flexible sheet.

15 Claims, 21 Drawing Sheets

METHODS AND APPARATUSES FOR FITTING AN OBJECT

CROSS-REFERENCE TO RELATED APPLICATIONS

This application claims a priority benefit from a PCT patent application No. PCT/US2015/012452 filed 22 Jan. 2015 with the same title, which in turn claims a priority benefit from a U.S. Provisional Patent Application No. 61/930,304 filed 22 Jan. 2014. Both patent documents are incorporated herein by reference in their respective entireties.

BACKGROUND

Aspects herein relate to linings for fitting to a body part, and methods of use.

A number of methods have been developed for fitting certain types of objects to corresponding body parts. In particular, there has been recent interest in developing efficient ways to fit prosthetic and orthotic devices to corresponding body parts in a manner that is more convenient and comfortable for the wearer.

Conventional methods for fitting a prosthetic device to a residual limb typically involve placing a flexible sheet over the residual limb and forming a mold of the residual limb based on an approximation of its shape from the flexible sheet. However, the imprecision that conventional sheets typically provide in estimating the complex shape of the residual limb often require multiple iterations of shaping and molding, which can be expensive and time-consuming.

SUMMARY

The inventors have appreciated that it would be beneficial to provide an improved lining that is able to fit to a body part in a way that is simple, convenient and effective. The lining may include a flexible sheet having a fluid impermeable outer portion that encloses an internal volume. A number of barriers are provided for forming a number of compartments within the internal volume. The barriers and/or compartments may be substantially secured in place within the internal volume. Depending on the desired application, the compartment(s) may exhibit any suitable pattern, shape, size, density, etc. A conformable material may be located and contained within the compartments. In some embodiments, the conformable material may be a granular material including a number of particles that may shift, flow or may be otherwise movable within each compartment. The barriers may be permeable to gas and/or liquid, though, the barriers may be impermeable to the conformable material.

The lining may also include a port that allows for a fluid (e.g., gas and/or liquid) to be supplied to or aspirated from one or more compartments within the internal volume. In various embodiments, aspiration of gas and/or liquid from the internal volume may limit both deformation of the conformable material (e.g., or shifting of the particles of granular material) and shape adjustment of the flexible sheet.

Accordingly, the lining may be flexibly placed over a body part so as to conform to the shape of the body part. When suitably positioned, gas and/or liquid may be aspirated from the compartments (e.g., via vacuum), causing the lining to harden from a compliant state to an increasingly rigid state, depending on the level of aspiration of gas/liquid from the internal volume.

In one embodiment, a lining for providing fitting to a body part is provided. The lining may include a flexible sheet including a fluid impermeable outer portion which encloses an internal volume. A plurality of gas-permeable barriers are provided within the internal volume such that the barriers divide the internal volume into a plurality of compartments. The compartments may be substantially secured in place within the internal volume. A conformable material may be located within the compartments. While the barriers may be permeable to gas, the barriers may be impermeable to the conformable material.

In another embodiment, a lining for fitting an object to a body part is provided. The lining may include a flexible sheet including a fluid impermeable outer portion which encloses an internal volume. The flexible sheet may be constructed and arranged to be placed between the body part and the object. The lining may further include a granular material including a plurality of particles located within the internal volume. The lining may include a port constructed and arranged for fluid to be supplied to or aspirated from the internal volume. Aspiration of fluid from the internal volume may limit both shifting of the granular material and shape adjustment of the flexible sheet.

In yet another embodiment, a method of installing a lining for fitting an object to a body part is provided. The method may include placing the lining over the body part such that an inner surface of the lining conforms to a shape of the body part. The lining may include a flexible sheet having a fluid impermeable outer portion enclosing an internal volume, a plurality of barriers forming a plurality of compartments within the internal volume, and a conformable material located within at least some of the plurality of compartments. The method may further include aspirating fluid from the plurality of compartments within the internal volume, wherein the aspiration of fluid may limit both deformation of the conformable material and shape adjustment of the flexible sheet.

Various embodiments of the present disclosure provide certain advantages. Not all embodiments of the present disclosure share the same advantages and those that do may not share them under all circumstances. Various embodiments described may be used in combination and may provide additive benefits.

Further features and advantages of the present disclosure, as well as the structure of various embodiments of the present disclosure are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Figure 1A:
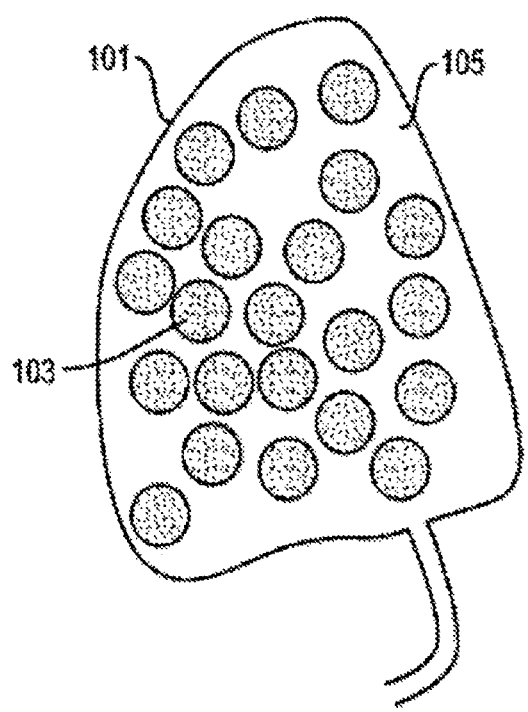
FIG. 1A depicts a schematic representation of a conformable material in a compliant state.

The present disclosure relates to a lining that includes a flexible sheet which contains a conformable material, for fitting an object to a body part. It can be appreciated that the lining may be separate from the object or part of the object itself. The conformable material may provide the ability for the lining to transition reversibly between a compliant state and a more rigid state. In the compliant state, the lining may be easily deformed and/or suitably conformable to the shape of the body part, whereas in the more rigid state, the lining may retain the particular shape that was formed while in the compliant state, while also providing a substantially greater amount of structural support than when the lining is in a more compliant state. For various embodiments, when a lining takes on a more rigid state, the lining is effectively made harder such that deformation is substantially limited. However, it can be appreciated that application of a sufficient amount of force may indeed result in a slight deformation of the conformable material, or lining.

As will be described in more detail below, the inventors have appreciated that linings in accordance with the present disclosure may be used in a variety of applications, and may be particularly advantageous in the field of prosthetics and/or orthotics. Such linings may provide an interface between a body part (e.g., residual limb, another part of the body) and an attachment portion (e.g., socket) of a prosthetic/orthotic device or other object, where the lining may be adjusted and re-adjusted multiple times, as desired. This ability to repeatedly adjust the structural conformation of the lining allows a user to accommodate changes in the size and/or shape of a residual limb and/or other body part which may occur during use.

The inventors have further recognized that it may be advantageous for the lining to include a number of compartments within which a conformable material is located. The compartments may serve to maintain the overall distribution of conformable material throughout the lining. The compartments may be formed from a plurality of barriers so as to be substantially secured in place within the lining. In some embodiments, the barriers may be permeable to gas and/or fluid, yet impermeable to the conformable material. Accordingly, while a gas or liquid may be permitted to migrate between compartments, the conformable material may be prevented or otherwise obstructed from such movement. That is, the conformable material may be confined within the boundaries provided by the compartments. By controlling or maintaining the overall distribution of the conformable material throughout the lining, issues such as settling, clumping and/or undesirable accumulation of the conformable material that would otherwise occur if the compartments were not present may be mitigated or reduced, allowing the lining to be reliably used in a variety of applications.

Aspects of various embodiments described herein may be suitable to overcome certain drawbacks related to the design and/or use of conventional systems which may utilize conformable materials to adopt and maintain the shape of an object. Specifically, in conventional systems, a conformable material is typically contained within a single large membrane or bag. Accordingly, such systems are unable to reliably maintain a uniform distribution of the conformable material throughout. For example, gravity or other outside forces may tend to cause settling, segregation, or clustering of the conformable media which can negatively affect certain functionalities such as shape capturing and/or structural integrity over time. Furthermore, the inventors have appreciated that the settling and segregation problems of conventional designs may become exacerbated in thin-sheet-like geometries, such as flexible linings, and may substantially limit their effectiveness or even prevent their use. For example, settling and segregation of conformable material in a thin-sheet-like geometry may leave large areas of the sheet devoid of the conformable material and thus those areas may contribute to poor performance or render such a lining unusable.

As discussed herein, embodiments of linings containing conformable material arranged according to aspects described herein may be particularly useful in prosthetic and orthotic applications, in which the complex shape of a body part may need to be matched with high precision. In conventional prosthetic and orthotic devices, fabricating a device to complement a wearer's unique physical geometry generally involves custom-made prosthetic sockets and orthotic supports which are made from, or reinforced by, hard materials which exhibit little to no compliance. While the particular shape of a body part such as a residual limb may be reproduced precisely during fabrication of a prosthetic device and/or socket through various casting and molding techniques, such body parts are often prone to natural fluctuations in the shape and volume of soft tissues due to various factors including, but not limited to, water retention, activity level, and weight gain or loss. These shape changes are not sufficiently addressed with existing materials and designs, as permanently rigid materials provide for very limited adjustability after manufacture and fitting. Furthermore, though some methods for allowing adjustability may be used (e.g., adjustable straps, inflatable bladders), such designs are in general unable to provide a desirable combination of adjustability through a controlled contour, ease of use, and stiffness or support for providing a suitable level of stability for a prosthetic or orthotic device.

Other advantages of the present disclosure may be apparent. For example, when in a compliant state, conformable material within a lining may be allowed to shift or deform to match the particular contours of a body part, and when in the more rigid state, the conformable material may provide the lining with a desirable amount of strength and/or stability. This may enable a lining to provide efficient load transfer and pressure redistribution between a body part and an associated device, such as a prosthetic socket or orthotic apparatus. For instance, conventional prosthetic linings that exhibit limited ability to provide mechanical support may have a tendency to stretch in a back and forth motion during use, leading to an occurrence commonly termed "milking." In such cases, the attachment between the prosthetic device and body part is not well formed or secured to a preferred amount of surface area, resulting in substantial discomfort and/or pain. Such an occurrence, when prolonged, may also result in tissue breakdown. In contrast, embodiments of the present disclosure provide a suitable degree of load transfer between the residual limb (or other body part), lining, and socket to which the wearable device is attached or coupled, resulting in a more natural feel for the wearer and improved tissue health.

In addition, as discussed herein, the conformable material may allow a lining to be repeatedly adjusted to accommodate changes in the shape of a body part, and/or the fit of a lining thereto, which may occur during use, for example due to natural fluctuations of the shape or volume of soft tissues. During use, the wearers' physical geometry typically changes shape, often resulting in a surface mismatch between the mounted device (e.g., prosthesis) and the soft tissue of the wearer (e.g., residual limb). In contrast with embodiments provided herein, a permanently rigid lining, or other conventional lining, is incapable of immediate mechanical re-adjustment, leading to insufficient support and, ultimately, discomfort for the wearer.

Various embodiments of the present disclosure may incorporate conformable materials, such as granular materials including a plurality of individual particles enclosed within flexible membranes. Such systems may allow for a reversible transition between compliant and more rigid states, for example, by applying vacuum to the system. Application of a vacuum may give rise to an increase in the overall density of the system which may, in turn, cause the particles comprising the granular conformable material to become "jammed" and act as a solid aggregate rather than as free-flowing individual particles which can be easily moved/shifted by the application of a slight force.

Figure 1B:
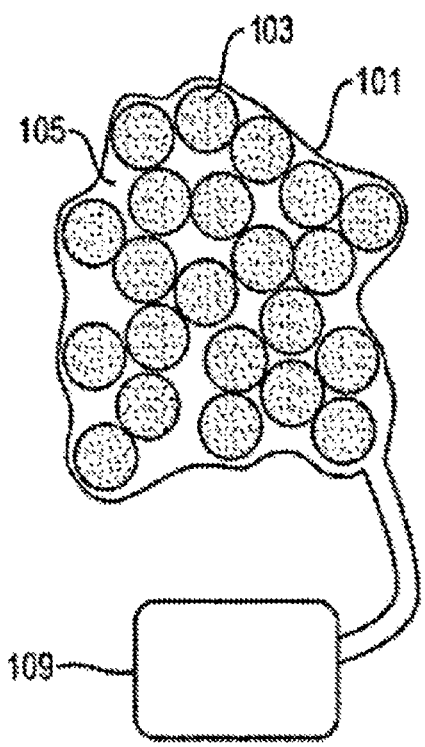
FIG. 1B shows a schematic representation of the conformable material of FIG. 1A in a more rigid state.

FIGS. 1A-1B depict an illustrative embodiment of such a system; in a first state (FIG. 1A), a collection of particles 103 contained within an impermeable flexible membrane 101 may have sufficient free volume 105 to move and flow and thus the system is compliant and may be formed into a desired shape. In a second state (FIG. 1B), the free volume 105 of the system is reduced, for example by application of vacuum with a pump 109, such that the particles 103 become "jammed" and the entire system becomes rigid, thus allowing the system to maintain the shape that was previously formed while in the compliant state. Upon release of the vacuum, the system may return to the "unjammed" state and may again undergo deformation, similar to that shown in FIG. 1A.

Figure 2:
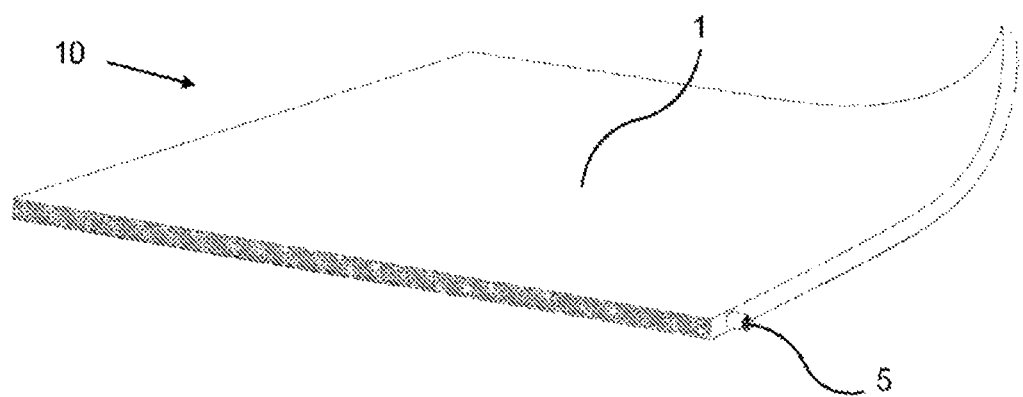
FIG. 2 is a perspective view of a lining in accordance with an embodiment.

According to certain aspects of the present disclosure, a lining may include a flexible sheet including a fluid impermeable outer portion or surface which encloses an internal volume. FIG. 2 depicts an illustrative embodiment of a lining 10, including a fluid impermeable outer portion 1, which may or may not include the exterior surface of the lining. That is, the fluid impermeable outer portion 1 may be coated or otherwise located underneath a material that may or may not be fluid impermeable. Though, the outer portion 1 itself may be sufficiently fluid impermeable such that a desired level of vacuum may be maintained within the internal volume. For example, in some embodiments, the outer portion may be capable of maintaining at least a partial vacuum for minutes, hours, days, weeks, months, or any other suitable amount of time, as the disclosure is not so limited.

In some instances, the outer portion may include a single impermeable sheet which may be folded over and attached to itself around the edge of the sheet, or alternatively it may include two or more impermeable sheets which are attached around a perimeter. The one or more sheets of the lining may be attached in any suitable manner according to any appropriate configuration such that the top and bottom surfaces of the lining enclose an internal volume which is sealed off from an external environment in a fluid-tight manner. Suitable attachment methods include, but are not limited to, solvent bonding, overmolding, RF heat sealing, and ultrasonic or heat welding, amongst others.

In the embodiment depicted in FIG. 2, the lining further includes a port 5 which provides fluid communication between an internal volume of the lining and an external apparatus. In some instances, the port may be connected to a pump which may be used to aspirate gas and/or liquid from the internal volume of the lining, to apply a desired level of vacuum thereto in reaching a jammed, more rigid state. The port may also be opened to allow gas and/or liquid to be supplied to or enter into the internal volume of the lining, hence, releasing the conformable material from the jammed state to a compliant state.

It can be appreciated that the port may include any appropriate structure or arrangement. For example, the port may include a valve that permits gas and/or liquid to flow therethrough when in an open position, and may obstruct flow through when placed in a closed position. The port may also be attached or otherwise coupled to a tube/conduit that provides for flow to and from the enclosed internal volume of the lining over an appreciable distance.

In some embodiments, while not expressly shown in the figures, one or more plumbing components may be integrated into the lining. The lining may house a number of pump and/or tube elements for routing fluid from the port to a vacuum component. For example, an elastomeric tube such as polyurethane or silicone tube over-molded, solvent bonded or RF welded to the lining may be integrated, embedded or otherwise placed adjacent to other structural features/materials of the lining.

The outer portion of the flexible sheet may include any suitable material. Depending on the particular embodiment, the outer portion 1 may be made from a robust and tear resistant material capable of withstanding repeated impact, friction, abrasion and/or elongation, and may have suitable material properties for a desired application. For example, for applications in which the outer portion may contact human skin, the durometer of the material may be in the range of 1-50 Shore A, inclusive, and may have elongation properties which complement that of human skin in order to reduce friction between the lining and skin.

In some embodiments, the outer portion may further include an elastic woven material embedded within and/or attached to an impermeable outer layer, which may provide for an enhanced level of strength and/or control over the directional stretching of the layer. In some embodiments, the outer portion of the lining may include woven or knit materials that are airtight and, thus, impermeable and/or resistant to abrasion. For instance, the outer portion of the lining may resist particular/granular material from undesirably cutting or wearing through the material. The outer portion may be made from any appropriate material, including, but not limited to, silicone, polyurethane, elastomer, woven and/or knit materials, natural and artificial rubbers, other elastic polymers, any other suitable material, or combinations thereof, as the disclosure is not so limited. In some embodiments, an outer portion of the lining may be coated with a composition that renders the outer portion of the lining impermeable.

Figure 3A:
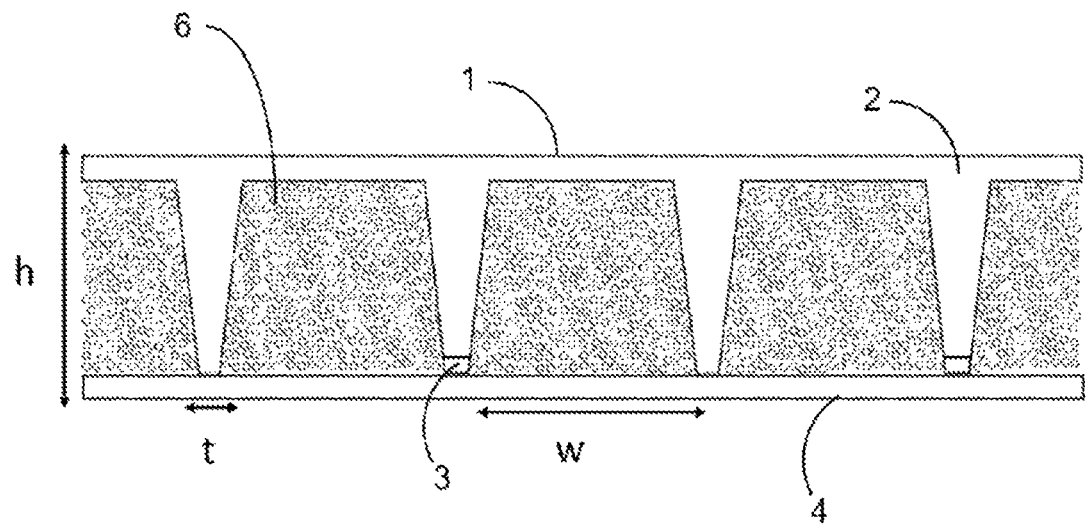
FIG. 3A depicts a cross-sectional view of a lining in accordance with an embodiment.

FIG. 3A depicts a cross-sectional view of one embodiment of a lining in accordance with the present disclosure. As shown, the lining includes a first flexible impermeable outer portion 1 and a second flexible impermeable outer portion 4. Each of the first outer portion and the second outer portion may be provided as surfaces of layers that are integrally formed, separately distinct and/or coupled together to form a seal between an internal volume and an external environment.

The lining may have a suitable height h. In some embodiments, the lining may have an average height h of greater than 0.1 mm, greater than 0.5 mm, greater than 1.0 mm, greater than 2.0 mm, greater than 5.0 mm (e.g., 5.0-35.0 mm), greater than 7.0 mm (e.g., 7.0-10.0 mm), greater than 8.0 mm, greater than 10.0 mm, greater than 12.0 mm, greater than 15.0 mm, greater than 20.0 mm, greater than 30.0 mm, greater than 40.0 mm, or greater than 50.0 mm; or less than 50.0 mm, less than 40.0 mm, less than 30.0 mm, less than 20.0 mm, less than 10.0 mm, less than 8.0 mm, less than 7.0 mm, less than 5.0 mm, less than 2.0 mm, less than 1.0 mm, or less than 0.5 mm. Combinations of the above-noted ranges, or values outside of the these ranges, may be possible for the average height of the lining. Though, it can be appreciated that the height h of the lining may substantially vary. For example, depending on the embodiment, some regions of the lining may have a relatively small height and other regions of the lining may have a comparatively large height. Such variation in height may be preferable for fitting to certain areas of the body which may have complex surface contours with wide variety.

As discussed herein, and shown in FIG. 3A, a conformable material 6 may be located within an enclosed internal volume of the lining. In some embodiments, the conformable material may comprise a granular material made up of a plurality of solid particles. Suitable granular materials may have a sufficient density of solid particles such that the granular material is able to freely shift and/or flow within a contained environment, and which may become jammed upon application of vacuum, as described herein.

In some embodiments, suitable granular materials may include particles of various shapes including, but not limited to, spheres, cubes, hollow or solid cylinders, sliced extrusions with triangular, U-shaped, or I-shaped cross-sections, other irregular shaped particles, or combinations thereof. A granular material may include particles which all have substantially identical shapes, or alternatively, the particles may have different shapes, as the disclosure is not so limited.

Depending on the particular embodiment, particles with a uniform or non-uniform size distribution may be used. Furthermore, the individual particles may have a characteristic size as small as 0.01 mm, and the size may be as large as the thickness of a lining. For example, in one embodiment, the particles may have an average size within a 60% difference, within a 50% difference, within a 40% difference, within a 30% difference, within a 20% difference, within a 10% difference, within a 5% difference, or within any other appropriate difference, of an average height h of a lining. However, other sizes may be suitable, as the disclosure is not so limited. In some embodiments, the average size of the particles of a granular material may be greater than 0.001 mm, greater than 0.005 mm, greater than 0.01 mm (e.g., 0.01-35 mm), greater than 0.1 mm, greater than 0.5 mm, greater than 1.0 mm, greater than 2.0 mm, greater than 5.0 mm, greater than 10.0 mm, greater than 15.0 mm, greater than 20.0 mm, greater than 30.0 mm, greater than 50.0 mm; or less than 50.0 mm, less than 30.0 mm, less than 20.0 mm, less than 10.0 mm, less than 5.0 mm, less than 2.0 mm (e.g., 1.0-1.5 mm, 1.0-2.0 mm), less than 1.0 mm (e.g., 0.5-1.0 mm), less than 0.5 mm (e.g., 0.1-0.5 mm), or less than 0.1 mm. Combinations of the above-noted ranges of the average particle size of the granular material may be possible, or values outside of the these ranges. The size of the particles may relate to the ability for the overall material to become more or less rigid during phase transition.

The particles comprising a granular material may be made from various materials such as fiberglass, polyethylene, elastomer, carbon fiber, aerogel, pumice, regolith, silica, metal, urea, acrylic, organic material, rigid foam, or any other suitable material, as the disclosure is not so limited. In some instances, granular particles may be custom manufactured using various processing techniques including injection molding, thermal forming, machining 3-D printing, or any other suitable technique. In some embodiments, granular materials may be configured so as to be able to form an interlocking structure. For example, the granular materials may suitably interlock when the lining enters the jammed, or more rigid, state.

Depending on the particular embodiment, the particles may have any suitable material properties, for example, an average durometer value in the range of 10 Shore A to 200 Shore A; however other particles with other hardness values may be suitable as the disclosure is not so limited. In some embodiments, the particles exhibit an average durometer of greater than 10 Shore A, greater than 50 Shore A (e.g., 60-110 Shore A), greater than 100 Shore A, greater than 150 Shore A, greater than 200 Shore A; or less than 200 Shore A, less than 150 Shore A, less than 100 Shore A, less than 50 Shore A, or less than 10 Shore A. Combinations of the above-noted ranges of hardness of the particles may be possible, or values outside of the these ranges. It can be appreciated that the material may influence the degree to which the granular material may shift, depending on how strong a vacuum is applied to the internal volume of the lining.

Additionally, non-granular materials that may be conformable in accordance with embodiments presented herein may be used. In some embodiments, such non-granular may include foams, gels, meshes, woven materials, interlocking solids, or other suitable materials, as the disclosure is not so limited. For example, in one embodiment, the conformable material may comprise a foam structure which collapses into or otherwise adopts a more rigid solid upon application of vacuum or other compressive stress. Alternatively, an interlocking solid which becomes rigid in one or more directions when compressed, or layers of rigid folded sheet material containing a plurality of creases which may interlock upon application of vacuum may be used in some embodiments. In another embodiment, a conformable material may comprise a foam containing rigid particles suspended within cavities which may be aspirated to collapse the foam around the particles. In view of the above, any suitable material may be used which may exhibit a reversible phase transition between a first, compliant state, in which the material may suitably conform to the shape of an object, and a second, more rigid state, in which the material may maintain the shape that was formed while in the previous compliant state. This ability of a conformable material to reversibly transition between the compliant and rigid states, within the confines of a flexible outer impermeable sheet/portion, allows the lining to be easily readjusted, as desired. In some cases, such adjustment may occur in the midst of use where a user and/or controller may cause the conformable material within the lining to phase transition between compliant and rigid states on demand and/or according to a desired fitting protocol. Or, the lining may be configured to be held in a more rigid state for a prolonged period of time (e.g., hours, days, weeks, months, years, etc.). For example, a vacuum may be held within the lining to maintain a more rigid or jammed state for such a prolonged period of time.

As provided herein, it may be beneficial to reduce or limit settling, clumping or segregation of the conformable material within a lining. Referring again to FIG. 3A, a plurality of barriers 2 may be included within a lining which, in some embodiments, extend transversely across the lining from a first outer portion of the lining on one side of the internal volume toward a second outer portion of the lining at an opposing side of the internal volume. As further shown, the barriers may segment the internal volume into a plurality of compartments in which the conformable material 6 is located. Furthermore, the barriers may be fixed, attached or otherwise secured in place, for example, to the outer flexible sheet/portion, to each other, etc., resulting in the compartments themselves being substantially secured in place within the internal volume of the lining. As a result, the compartments, and the conformable material within the compartments, may remain in substantially the same location relative to the outer portions of the lining. Such a structure may maintain the conformable material distributed relatively evenly throughout the lining.

Depending on the particular embodiment, the barriers 2 may be integrally formed on one or both of the first outer portion 1 and the second outer portion 4 of the lining. For example, FIG. 3A depicts an embodiment of a lining in which the barriers 2 are integrally formed with the first outer portion 1 of the lining, and the barriers 2 are attached or otherwise coupled to the second outer portion 4. It can be appreciated that the barriers are not required to be integrally formed with the outer portion(s), surface(s) or sheet(s) and may be suitably attached in an appropriate manner. The barriers 2 further include passages 3 which may allow for gas and/or liquid to pass therethrough, yet impermeable to the conformable material.

Figure 3B:
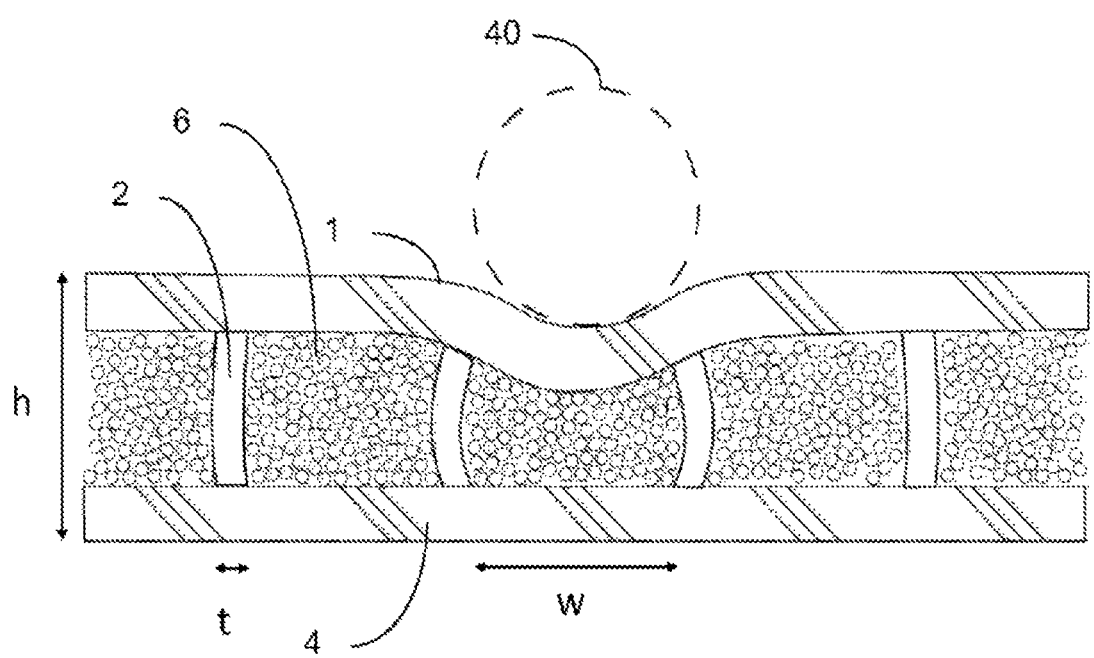
FIG. 3B illustrates a cross-sectional view of another lining in accordance with an embodiment.

FIG. 3B shows another embodiment of a lining having flexible impermeable outer portions 1, 4 and barriers 2 that define compartments containing a conformable material 6. In this embodiment, the barriers 2 include a porous material that may be gas permeable, yet is impermeable to the conformable material 6. For example, the maximum pore size of the porous barriers may be smaller than the minimum particulate size of the conformable/granular material. In this embodiment, the lining is in a compliant state, and is subject to indentation by an external object 40. As a result, the outer portion 1 flexes inward and the barriers flex outward to accommodate the external load. The conformable material 6 also shifts accordingly. In some embodiments, the external object 40 may be a protrusion on a body part having a shape to which the lining may conform. Thus, once the lining matches the contour of the external object 40, the lining may then be placed in a more rigid (jammed) state (not expressly shown) so as to provide mechanical support for the object 40.

Figure 3C:
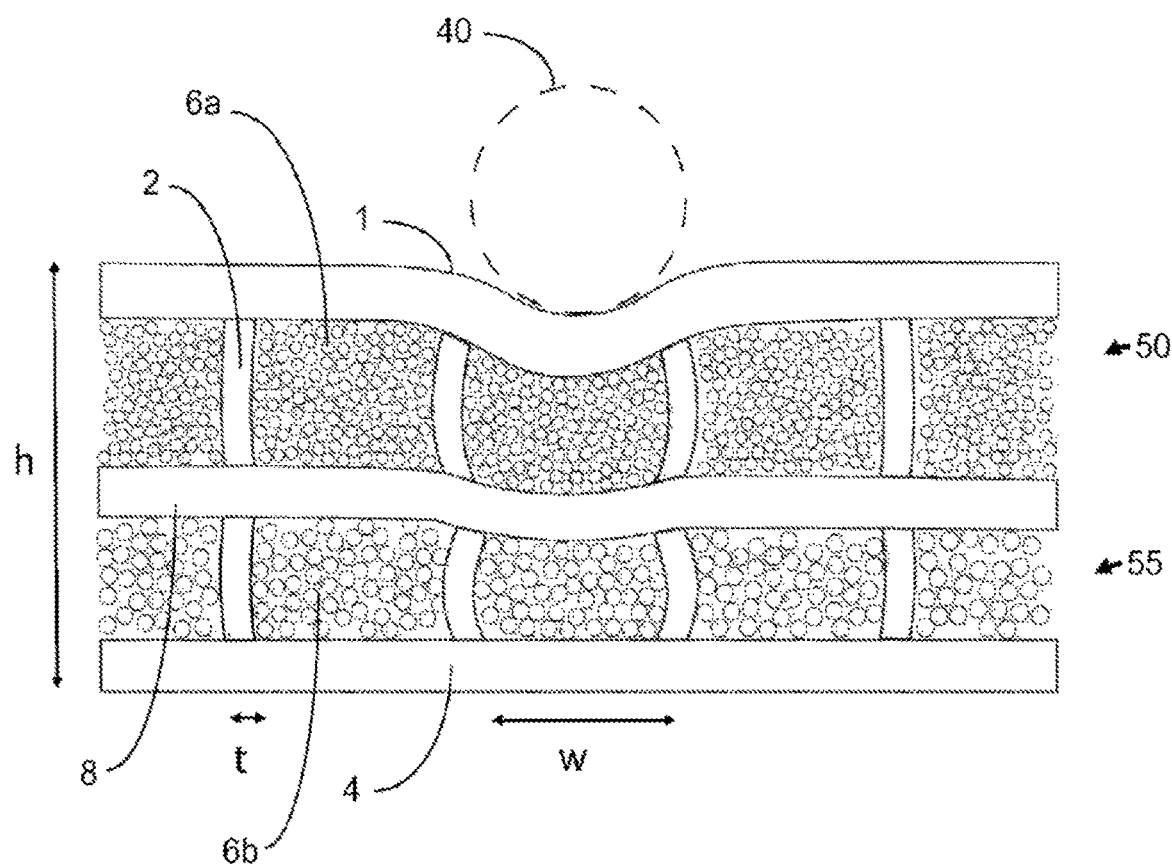
FIG. 3C depicts a cross-sectional view of another lining in accordance with an embodiment.

FIG. 3C illustrates another embodiment of a lining having two layers 50, 55, similar to that shown in FIG. 7 below. This lining includes flexible impermeable outer portion 1, 4, flexible intermediate portion 8 and barriers 2 that define compartments containing conformable materials 6a, 6b. That is, the first layer 50 includes conformable material 6a contained between outer portion 1 and intermediate portion 8, and the second layer 55 includes conformable material 6b contained between outer portion 4 and intermediate portion 8. As discussed further below, it may be beneficial for the lining to include multiple layers, for example, to provide an additional level of adjustability for the overall lining. Here, the external object 40 is pressed up against the lining, resulting in compliance of both the first and second layers 50, 55 to accommodate the load. Similar to that described for FIG. 3B, when the lining suitably matches the contour of the external object 40, the first and/or second layer of the lining may be placed in a more rigid state, providing mechanical support for the object 40. As further shown, the average particle size of the material 6b is larger than the average particle size of the material 6a, which may result in variation of the overall mechanical stability between layers 50, 55 for a given level of vacuum.

In some embodiments, while not shown in the figures, the lining may include a support structure such as a scaffolding, lattice or truss for supporting and/or distributing the conformable material throughout respective compartments. For example, when in a more compliant state, the conformable material may collect on and/or around various regions of the support structure, providing the lining with a pre-formed structure for fitting the lining to a body part. In some cases, the support structure may include a material that attracts the conformable material, for suitable distribution thereof throughout each of the compartments, for example, so that when a vacuum is applied, transition to a more rigid state occurs more readily than would otherwise be the case without the support structure.

In some embodiments, the support structure is collapsible or otherwise relatively pliable when the lining is in a compliant state, or under only a small amount of force.

Though, upon exposure to a greater degree of compressive force, the support structure is configured to exhibit increasingly more rigid behavior.

In certain embodiments, the lining may include an external support structure that is configured to interlink or otherwise couple with the conformable material when the lining phase transitions to a more rigid state. For example, the conformable material may further conform to a scaffolding or other support structure located exterior to the outer portion(s)/sheet(s) of the lining. In some cases, such coupling may provide for an added level of suspension or support for the system during use.

Figure 4:
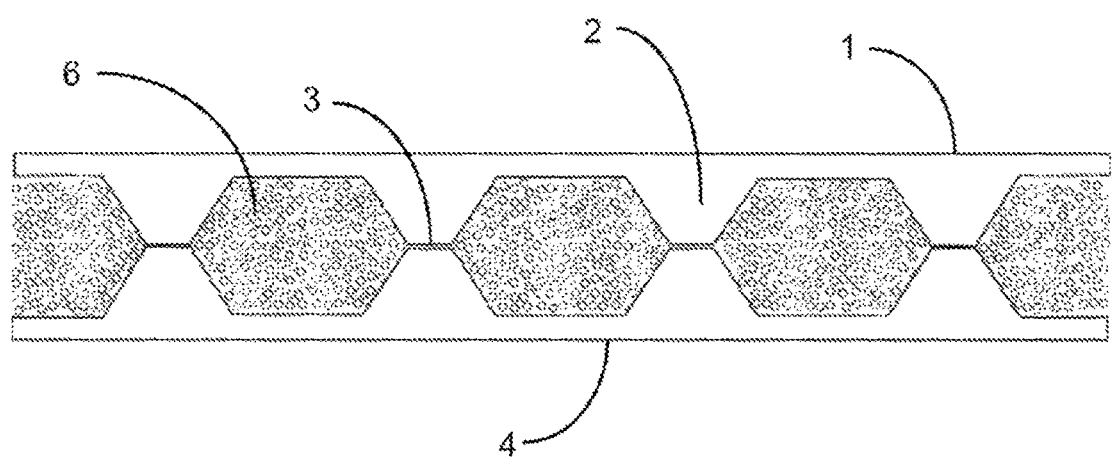
FIG. 4 shows a cross-sectional view of another lining in accordance with an embodiment.

FIG. 4 depicts another embodiment in which portions of the barriers 2 are integrally formed with each of the outer portions 1 and 4, and extend toward one another. As shown, the portions of the barriers, or barrier elements, are mutually aligned to form a barrier 2 that extends across the internal volume of the lining from one side to the opposite side. In this embodiment, the passages 3 of the barriers 2 are located where the barrier elements, integrally formed with the flexible impermeable outer portions 1, 4 meet.

Figure 5:
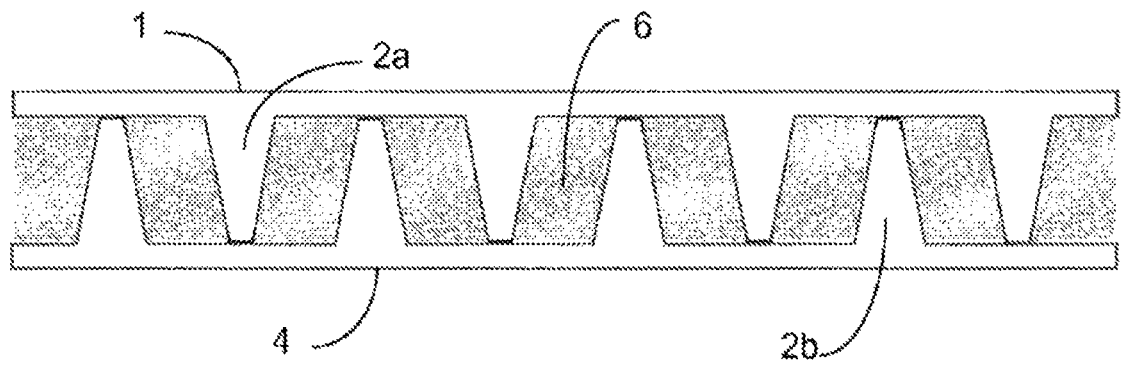
FIG. 5 illustrates a cross-sectional view of yet another lining in accordance with an embodiment.

FIG. 5 depicts yet another embodiment in which barriers 2 are integrally formed in an alternating configuration with each of the flexible impermeable outer portions 1, 4. That is, in this embodiment, barriers 2a extend from the first outer portion/sheet 1 transversely across the internal volume of the lining toward the second outer portion/sheet 4, and barriers 2b extend from the second outer portion/sheet 4 transversely across toward the first outer portion/sheet 1. As shown, the barriers 2a, 2b are misaligned so as to form separate and distinct compartments therebetween. In each of the embodiments disclosed herein, the barriers may be attached to one or more outer portions and/or sheets via any suitable method such that the barriers are substantially secured in place relative to the outer surface layers. In this embodiment, passages 3 are also located at the attachment points between the barriers and the respective flexible impermeable outer portions.

As provided herein, the barriers may be constructed such that they are substantially impermeable to the conformable material, so as to suitably confine the conformable material within respective compartments. Yet, the barriers may be permeable to gas, e.g. air, to enable facile removal and/or introduction of air into to the internal volume, to control the state (e.g., compliant, rigid) of the conformable material. For example, the barriers may be made from a gas-permeable material such as an open cell foam containing pores with a maximum size that is less than the minimum size of the particles which may comprise the conformable material. In various embodiments, the barriers may also be permeable to liquid, yet impermeable to the conformable material. In some cases, the barriers are breathable, for example, permeable to gas, yet impermeable to liquid.

Depending on the particular embodiment, a barrier comprising a permeable material may have a suitable average pore size. In some embodiments, the average pore size of one or more barriers of the lining may be greater than 0.001 mm, greater than 0.005 mm, greater than 0.01 mm, greater than 0.1 mm, greater than 0.5 mm, greater than 1.0 mm; or less than 1.0 mm, less than 0.5 mm, less than 0.1 mm (e.g., 50-100 microns), less than 0.05 mm (e.g., 10-50 microns), less than 0.01 mm, less than 0.005 mm, or less than 0.001 mm.

Combinations of the above-noted ranges, or values falling outside of these ranges, may be possible for the average pore size of the barriers.

Alternatively, for some embodiments, the barriers may include a fluid or gas impermeable material which includes passages and/or valves that extend and provide for fluid or gas transport therethrough. For example, in the embodiments depicted in FIGS. 3 and 4, at least some or all of the barriers 2 may include passages 3 to provide fluid communication between adjacent compartments. In some embodiments, the passages 3 may be sized to allow gas (e.g. air) to pass through but to prevent the migration of conformable material 6 (e.g., granular particles, gel) between compartments.

Embodiments of the barriers may include any suitable material. In some embodiments, the barriers may include a flexible material, an elastic material, a foam, a polymer, a porous material, a woven material, a breathable material, sponge, cork, knit, or any other suitable material, as the disclosure is not so limited.

Figure 6:
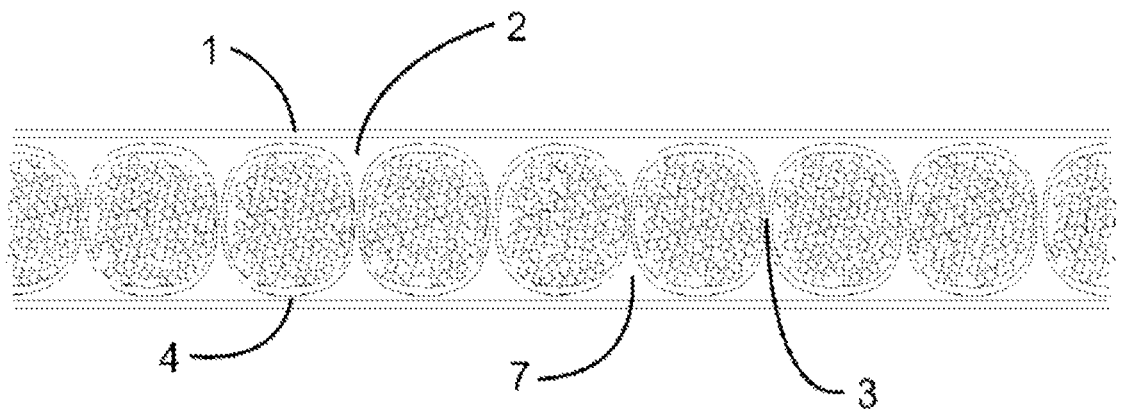
FIG. 6 shows a cross-sectional view of another lining in accordance with an embodiment.

In some embodiments, a series of compartments may be formed by a single sheet of a fluid and/or gas permeable material, which may itself be secured within an internal volume of a lining. For example, FIG. 6 depicts an embodiment of a lining in which the internal compartments containing conformable material 6 are formed within a gas-permeable material 7. In some cases, such a material 7 is a knit and/or woven material (e.g., quilted material, stretchable fabric) that encapsulates the conformable material. In some embodiments, compartments may be formed so as to exhibit a bubble-like configuration, with the conformable material located therein. Such an embodiment may further include passages 3 and/or valves between adjacent compartments. Depending on the particular embodiment, the barriers 2 may be gas-permeable, yet may prevent or obstruct the flow and passage of liquids and/or solids. Or, the barriers may be gas- and liquid-permeable, but impermeable to solid particles. Alternatively, the material 7 may be an open cell foam, as discussed above.

In view of the above, any suitable structure capable of confining conformable material while maintaining gas permeability may be used, as the disclosure is not so limited.

In some embodiments, the lining may include an open cell foam material that is surrounded by an impermeable skin or layer. The impermeable skin or layer may or may not be attached to the open cell foam, and may be suitable to maintain an airtight seal between the internal volume and the external environment.

The state of the conformable material within a lining may be controlled by selectively supplying to or aspirating fluid from the plurality of compartments within a lining through a port 5 (FIG. 2). For example, sufficient aspiration of fluid and/or gas from the plurality of compartments may obstruct deformation or flow of the conformable material so as to cause the conformable material to transition to a more rigid, jammed state; this may also prevent or otherwise limit the ability for the lining to be adjusted in shape. Subsequently, supply of fluid and/or gas to the plurality of compartments may then permit deformation or flow of the conformable material so as to allow the conformable material to transition to a compliant state; which may allow the lining to be adjusted in shape. As discussed herein, it can be appreciated that this process of aspirating fluid to make the conformable material and the lining more rigid, and later supplying fluid to return the conformable material and lining to a more flexible state (e.g., allowing particles to shift in position relative to one another), may be repeated any suitable number of times to allow for reshaping and/or readjusting of the lining.

In some embodiments, each of the internal compartments of the lining may be connected with one another as well as with a port 5, allowing for aspiration of gas from the entire internal volume of the lining and/or supply of gas thereto. However, in some embodiments, the compartments may not all be connected, as the disclosure is not so limited. For example, in one embodiment, the internal volume of a lining may include of a plurality of compartments, separate from one another, and which may not be in fluid communication with each other. In some cases, compartments that are in fluid communication with one another may be grouped together, and may be arranged so as not to be in fluid communication with other separate groups or clusters of compartments. The lining may further include a number of ports that each correspond to the various groups of compartments. Accordingly, the conformable material contained in each group of compartments may be independently transitioned between the compliant and more rigid states. Such arrangements may be advantageous as they may allow for linings to have separately adjustable regions, for example, to allow and/or constrain range of motion of the object to which the lining is conformed/fitted.

Although the figures depict arrangements of compartments in a single layer, other configurations may also be used, as the disclosure is not so limited. For example, in one embodiment, a lining may comprise two or more layers of compartments containing conformable material, for example, with a gas-permeable barrier disposed between the layers. Such an arrangement may allow for the use of thicker linings which may be able to provide a greater degree of support, while still preventing or reducing settling or segregation of the conformable material within the lining.

In some applications, it may be advantageous to provide a lining containing two or more conformable materials which may have different material properties and/or which may independently be able to be transitioned between compliant and more rigid states. For example, FIG. 7 depicts an embodiment of a lining comprising two overlapping layers 50, 55: a first layer 50 formed by a first flexible impermeable portion 1 and a second flexible impermeable portion 4, and containing a first conformable material 6a; and a second layer 55 formed between a third flexible impermeable portion 8 and a fourth flexible impermeable portion 9, and containing a second conformable material 6b. Such an embodiment may be advantageous for prosthetic lining applications in which a two-stage fitting and adjustment process may be desirable, as will be described in more detail below.

The barriers described herein may be constructed and arranged to exhibit a suitable degree of elastic relief, to allow for bending of the lining. For example, the barriers may be configured to elongate and/or contract as the lining is flexed. Such a design may provide for an enhanced range of motion for the lining so that the barriers are less prone to mechanical failure such as tearing or separation from the impermeable outer portion to which the barriers may be attached. In one embodiment, the barriers may feature a corrugated structure such as a spring or oscillating geometry (e.g. wave structure) which may absorb tensile and/or compressive deformation without risk of failure, or transferring a significant amount of force to other regions of the lining. In such an embodiment, the amplitude, frequency and overall length of the corrugated structure may be chosen to permit a desired range of extensibility, including allowing a lining to fold back upon itself without rupturing the internal barriers and maintaining separation of conformable material between compartments.

Depending on the particular embodiment, the characteristics of the corrugated structure may or may not be continuous within a single barrier, as the disclosure is not so limited. For example, a corrugated barrier structure may feature a wavelength and/or amplitude which are constant along a particular barrier to form a regular corrugated structure, or alternatively, the values may vary along the barrier. Furthermore, the properties of the corrugated structure may be varied at different locations in a lining to allow for different portions of the lining to have different bending characteristics or flexibilities. For example, a more flexible or extensible corrugated structure may be implemented in areas of a lining which are expected to experience larger bending deformations. In some embodiments, the corrugated structure of a barrier may extend along the planar direction of the lining and/or transversely across the height of the lining.

Figure 8A:
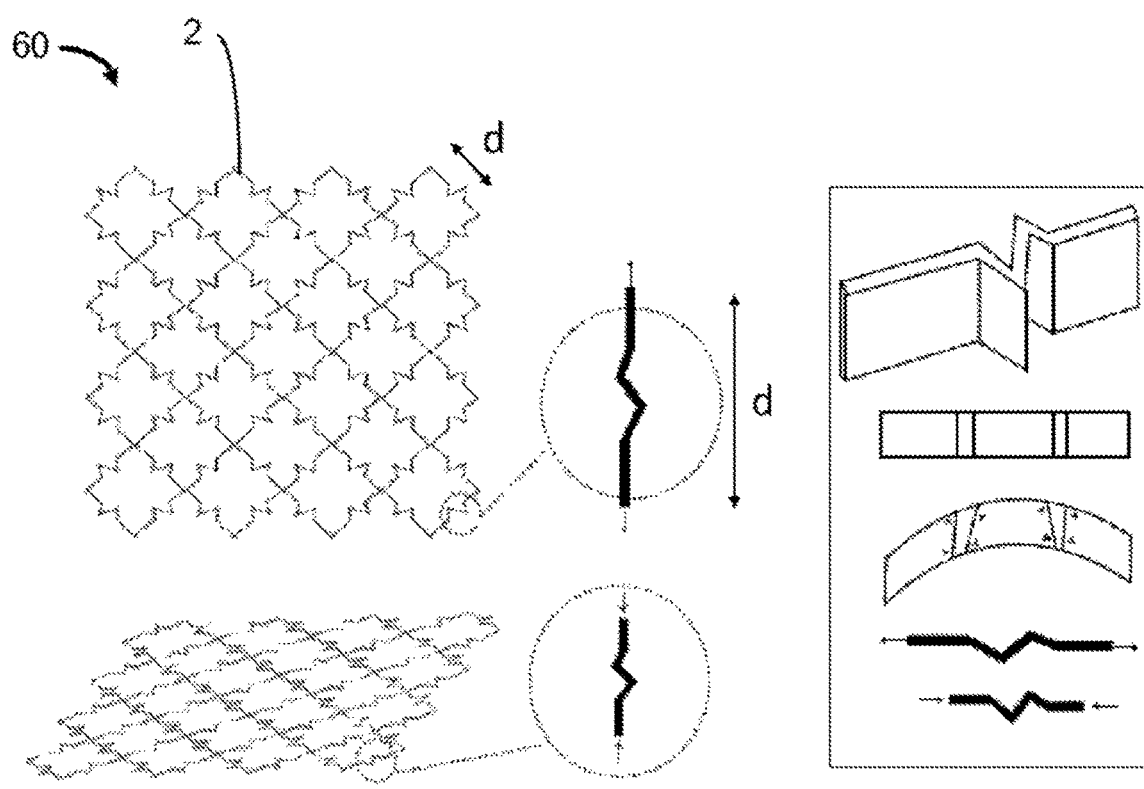
FIG. 8A illustrates a top view of compartments of a lining in accordance with an embodiment.

FIG. 8A shows a top view of an example of a group of compartments 60 separated by barriers 2 that are structured so as to provide such elastic relief, as the barriers 2 may suitably be lengthened or may contract, as desired. In some embodiments, a barrier according to aspects described herein may have a total length along the planar direction of the lining that is longer than the actual distance d traversed by the barrier along that planar direction. In some cases, the distance d may be equivalent to the width w of a compartment and/or the distance between intersection points of different barriers. As apparent from FIG. 8A, the barrier along the planar direction is substantially straight when the total length of the barrier along the planar direction of the lining approximates the actual distance d traversed by the barrier along that planar direction. In some embodiments, the total length of the barrier along the planar direction is more than 2 times greater, more than 3 times greater, more than 4 times greater, more than 5 times greater, more than 10 times greater, more than 15 times greater, more than 20 times greater, more than 25 times greater, more than 30 times greater, or more than 40 times greater than the actual distance d traversed by the barrier. In some embodiments, the total length of the barrier along the planar direction is less than 40 times greater, less than 30 times greater, less than 20 times greater, less than 10 times greater, less than 5 times greater, less than 3 times greater, or less than 2 times greater than the actual distance d traversed by the barrier. It can be appreciated that combinations of the above-noted ranges, or values outside of these ranges, may be possible.

One or more barriers 2 may include a relatively corrugated or wave-like structure, which provides additional space for the barrier to stretch and/or become more compact when the overall lining is bent or deformed. Accordingly, upon stretching of certain portions of the lining such that the distance d traversed by the barrier increases, the added length provided by the corrugation allows the barrier to easily elongate relative to its initial state. On the other hand, upon aggregation or clustering of various regions of the lining such that the distance d traversed by the barrier is reduced, the barrier may contract relative to itself, similar to an accordion, increasing the overall frequency of the corrugation. In some embodiments, a barrier may have biasing characteristics, exhibiting substantially elastic properties, where upon release of the lining from a bent or otherwise flexed state, the barrier may have a tendency to revert or spring back to its initial, non-deformed position.

As a result, barriers in accordance with the present disclosure may be flexible and/or stretchable so that the lining may suitably elongate and/or contract as it rolls over itself, without disrupting the ability for the compartments, and the conformable material located therein, to undergo phase transition in a desirable manner (e.g., between jammed and non-jammed states). In certain instances, such characteristics may be particularly beneficial, for example, when wrapping a lining around a body part, where significant roll-over of the lining occurs.

Depending on the particular embodiment, the compartments and patterned structure(s) thereof may have any suitable width or characteristic size. In some embodiments, the average width w of the compartments may fall within the same ranges as those provided herein with respect to the average height h of the lining, or compartments thereof. For example, in one embodiment, the compartments may have a width w or an inscribed circular diameter ranging of 1 mm to 50 mm, inclusive, and the height of the compartments, which may correspond to the height h of a lining, may also be in the range of 1 mm to 50 mm, inclusive. In some embodiments, the average width of the compartments may be greater than 0.1 mm, greater than 0.5 mm, greater than 1.0 mm, greater than 5.0 mm, greater than 10.0 mm, greater than 15.0 mm, greater than 20.0 mm, greater than 30.0 mm (e.g., 5-35 mm), greater than 40.0 mm, greater than 50.0 mm; or less than 50.0 mm, less than 40.0 mm, less than 30.0 mm, less than 20.0 mm, less than 10.0 mm, less than 5.0 mm, less than 1.0 mm, or less than 0.5 mm. Combinations of the above-noted ranges, or values outside of the these ranges, may be possible for the average width of the compartments within the lining.

Barriers in accordance with the present disclosure may have any suitable thickness t. In some cases, and as shown in a number of figures, one or more barriers may have a tapered shape as they extend across the lining. As provided herein, the thickness t of a barrier may be determined by the average thickness along the distance of the barrier extending between opposite sides of the lining. In various embodiments, the average thickness of the barriers separating adjacent compartments may be in the range of 0.01 mm to 10 mm, inclusive. Alternatively, in some embodiments the barrier thickness may be less than 0.01 mm or greater than 10 mm, or may be in any combination of the ranges disclosed herein, as the disclosure is not so limited. In some embodiments, the average thickness of the barriers may be greater than 0.01 mm, greater than 0.05 mm (e.g., 0.05-4.0 mm), greater than 0.1 mm, greater than 0.5 mm, greater than 1.0 mm, greater than 1.5 mm, greater than 2.0 mm, greater than 5.0 mm; or less than 10.0 mm, less than 5.0 mm, less than 2.0, less than 1.5 mm, less than 1.0 mm, less than 0.5 mm, less than 0.1 mm, or less than 0.05 mm. Combinations of the above-noted ranges may be possible, or values outside of the these ranges.

Compartments and barriers described herein may exhibit any appropriate volume. In some cases, it may be preferable for the barrier to be as thin as possible, to provide a suitable amount of space within the compartments for the conformable material to be located, yet the barriers should also be strong or thick enough to maintain structural integrity of each of the compartments. Accordingly, as the volume of the compartments increases, the volume and/or thickness of the barriers between such compartments are also likely to increase, so that the system continues to have mechanical stability. In some embodiments, an average volume ratio between the barriers and the compartments of the lining may be greater than 1:5, greater than 1:10, greater than 1:15, greater than 1:20, greater than 1:30, greater than 1:40, greater than 1:50, greater than 1:60, greater than 1:70, greater than 1:80, greater than 1:90, greater than 1:100, greater than 1:150, greater than 1:200, greater than 1:250, greater than 1:300, greater than 1:350, greater than 1:400, greater than 1:450, greater than 1:500; or less than 1:550, less than 1:500, less than 1:400, less than 1:300, less than 1:200, less than 1:100, less than 1:80, less than 1:50, less than 1:20, or less than 1:10. Combinations of the above-noted ranges may be possible, or values outside of these ranges.

The inventors have further appreciated that the mechanical performance and overall comfort provided by a lining may be influenced by arranging the compartments of the lining according to a pattern. Various patterns of compartment shapes, when viewed from the top of a lining, may include certain polygons with features that are convex or concave, equilateral or non-equilateral, equiangular, non-self-intersecting and simple shapes, and comprising acute or obtuse angles. Alternatively, suitable patterns may include, for example, circles, symmetric or non-symmetric shapes, oval or ellipsoidal shapes, dog bone shapes, or any other suitable shape or combination of shapes, as the disclosure is not so limited. For example, in one embodiment, the compartments may be substantially hexagonal. In another embodiment, the compartments may include an irregular or amorphous structure in which each compartment has a unique shape.

The dimensions of the compartments and barriers may be uniform, or alternatively, they may vary at different locations within a lining. For example, in one embodiment, the patterned structure of a lining may include a first region having a first density of compartments and a second region having a second, smaller density of compartments. A lining having regions with different area or volume densities of compartments may allow for the mechanical performance (e.g. rigidity) of the lining to be tuned to have a desired response in a specific location. For example, a higher area or volume density of compartments may be located in regions which may be exposed to higher forces or stresses, or in regions in which it may be desirable to provide additional rigidity and mechanical support.

It may be desirable for the lining to resist or facilitate folding along a particular direction. In some embodiments, the pattern of compartments may form lines along the planar direction of the lining that may encourage or resist folding there along. For example, when in a suitably compliant (non-jammed) state, to more precisely conform to a certain part of the body, it may be preferable for the lining to be able to be folded, bent or otherwise flexed along a particular direction. Accordingly, the compartments may be patterned so as to form one or more crease lines along the lining, where displacement is readily able to occur. Alternatively, for some embodiments, when in a more rigid (jammed) state, to maintain the mechanical integrity and stability of the adopted shape of the lining, it may be preferable to suppress the tendency for folding to occur at certain portions of the lining. As a result, the compartments may be patterned so as to form one or more fault lines along the lining, where displacement is less likely to occur.

Figure 8B:
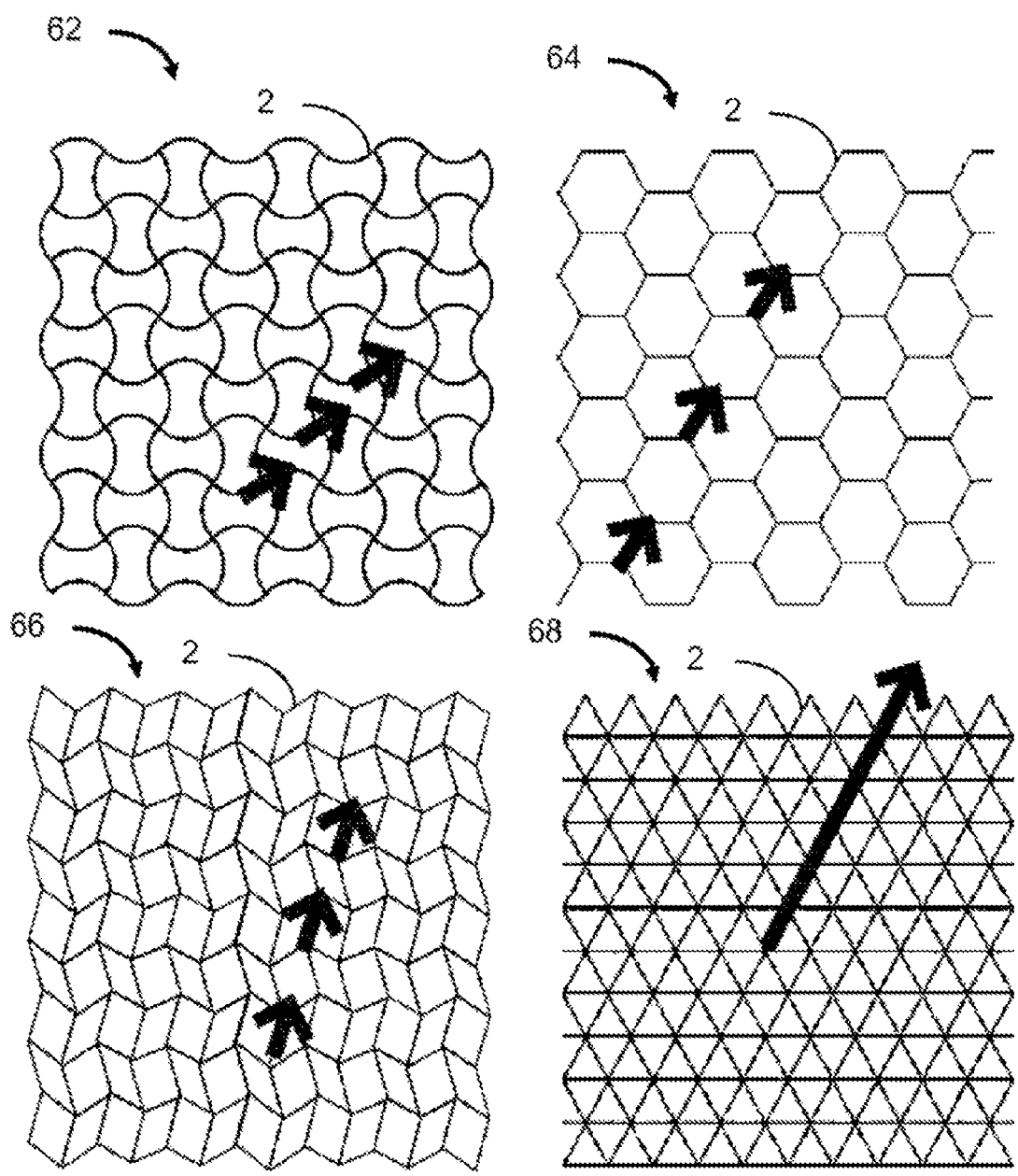
FIG. 8B depicts various top views of compartments of various linings in accordance with some embodiments.

FIG. 8B illustrates various embodiments of a number of compartments, and barrier walls thereof, formed into patterns 62, 64, 66, 68 which may facilitate or resist folding along the respective directions depicted by the arrows. While it can be appreciated that embodiments of the present disclosure may incorporate any suitable pattern of compartments, the compartments of pattern 62 are shaped according to a dog-bone type structure, the compartments of pattern 64 include a hexagonal packed structure, and the compartments of pattern 66 include a parallelogram type structure. In each of patterns 62, 64, 66, the compartments are arranged such that folding is resisted along the direction indicated by the three short arrows (i.e., fault line), particularly when the lining is placed in a more rigid (jammed) state. However, in pattern 68, the compartments are arranged to facilitate folding along the direction indicated by the long arrow (i.e., crease line), for a preferred level of flexibility, particularly when the lining is placed in a compliant (non-jammed) state. It can be appreciated that other arrangements are possible for patterns of compartments that form fault and crease lines. In some embodiments, layers of folded sheet material may be stacked on top of each other, and may further arranged to interlock upon transition of the lining from a compliant state to a more rigid state.

Figure 8C:
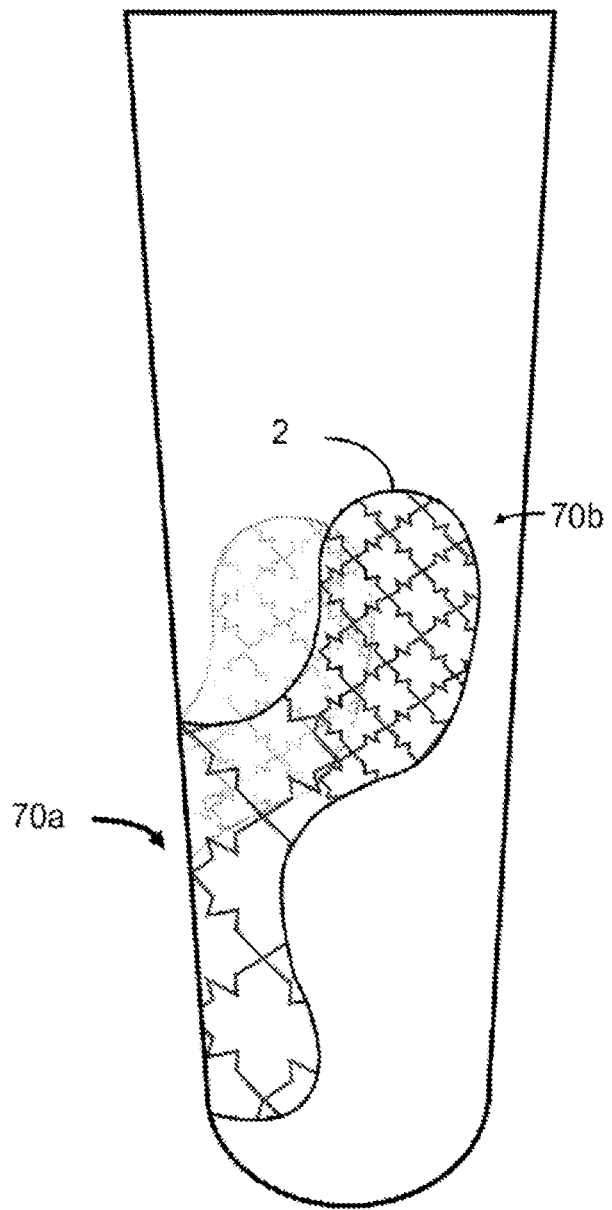
FIG. 8C shows a plan view of compartments of a lining fit on to a body part in accordance with some embodiments.

As also discussed herein, linings in accordance with the present disclosure may have barriers and compartments that vary in size. FIG. 8C depicts an embodiment of a lining that includes a first group of compartments 70a and a second group of compartments 70b where the respective sizes and shapes of the barriers and compartments of each group 70a, 70b is different. As shown, the compartments of the first group 70a are larger than the compartments of the second group 70b. That is, the density of compartments of the first group 70a is less than the density of compartments of the second group 70b. In accordance with the present disclosure, such variation in size and density of compartments may be preferable, for alignment of the lining with particular regions of the anatomy which may be expected to experience a greater or lesser degree of mechanical stress. Thus, the type, size, shape, density of compartments in particular regions of the lining may suitably correspond to the body part that is to be fitted.

A lining according to aspects of the present disclosure may be bent, rolled or otherwise flexed so as to take on any suitable structure. It can be appreciated that, in its compliant state, the lining may take on any appropriate shape. And, upon reaching the preferred shape, the lining may take on a more rigid or hardened state, for example, by vacuum aspiration.

Figure 9:
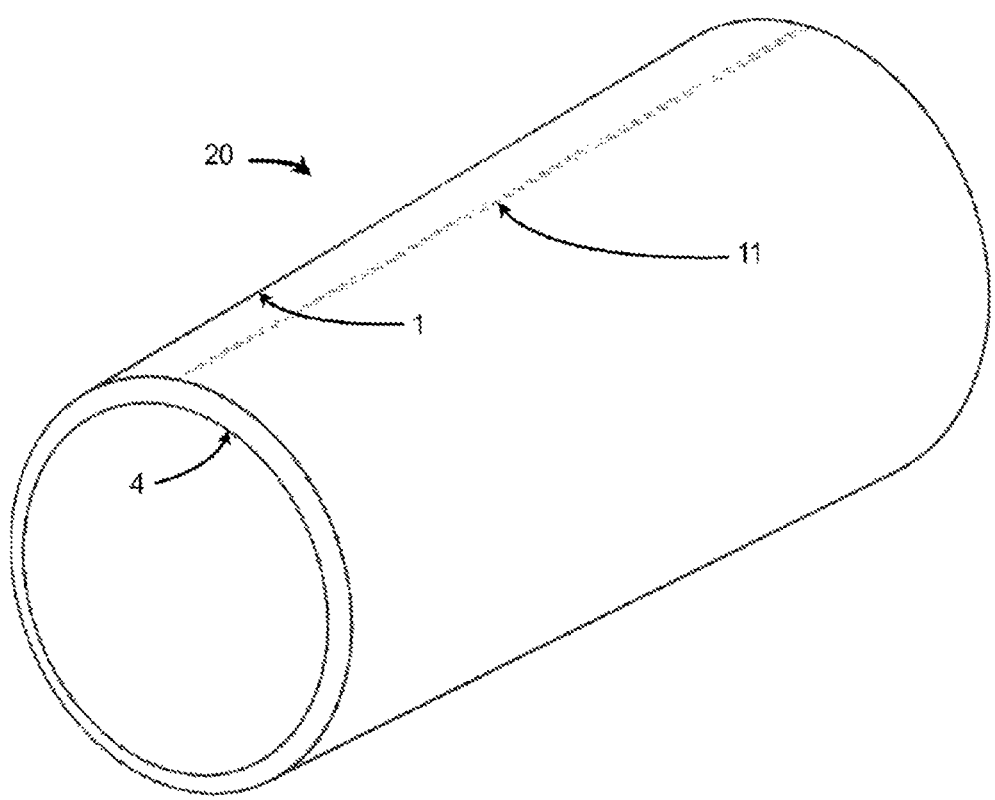
FIG. 9 shows a perspective view of a lining arranged as a tube in accordance with an embodiment.

In an embodiment depicted in FIG. 9, a lining may be rolled into a flexible tube 20. In such an embodiment, a first fluid impermeable outer portion 1 may form the exterior of the tube 20, and a second fluid impermeable portion 4 may form the interior of the tube. A seam 11 may be included in some embodiments, however embodiments in which the tube is formed without a seam are also contemplated.

Figure 10:
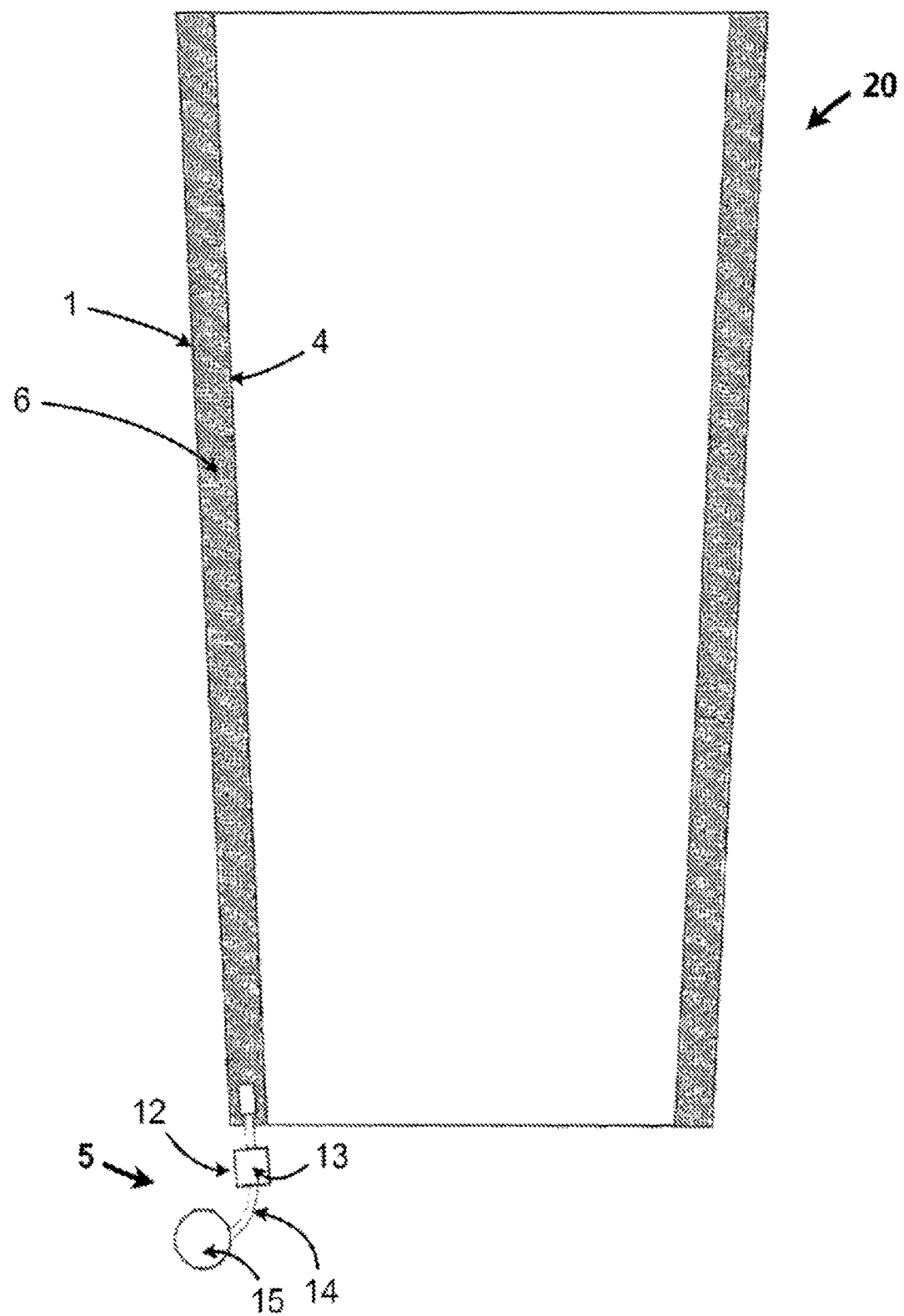
FIG. 10 depicts a cross-sectional view of a lining arranged as a tube in accordance with an embodiment.

FIG. 10 shows a schematic cross section of an illustrative embodiment of the lining where the interface 5 includes a vacuum port comprising a closable fitting 12 with a filter 13. A tube 14 connects the vacuum port 5 to a vacuum pump 15. The vacuum pump 15 may be a powered pump such as an electrical air pump or may be a manual pump such as a manually-squeezable bulb; depending on the particular embodiment, the vacuum pump 15 may be detachable from the lining, or alternatively it may be integrally formed with the lining 20 or in a separate component of a system in which the lining is used. As discussed above, it can be appreciated that a variety of plumbing components, such as tubes, conduits, valves, pumps, etc. may be incorporated within the lining in any suitable arrangement. For example, the plumbing components may extend throughout the lining and/or outside of the lining.

Figure 11:
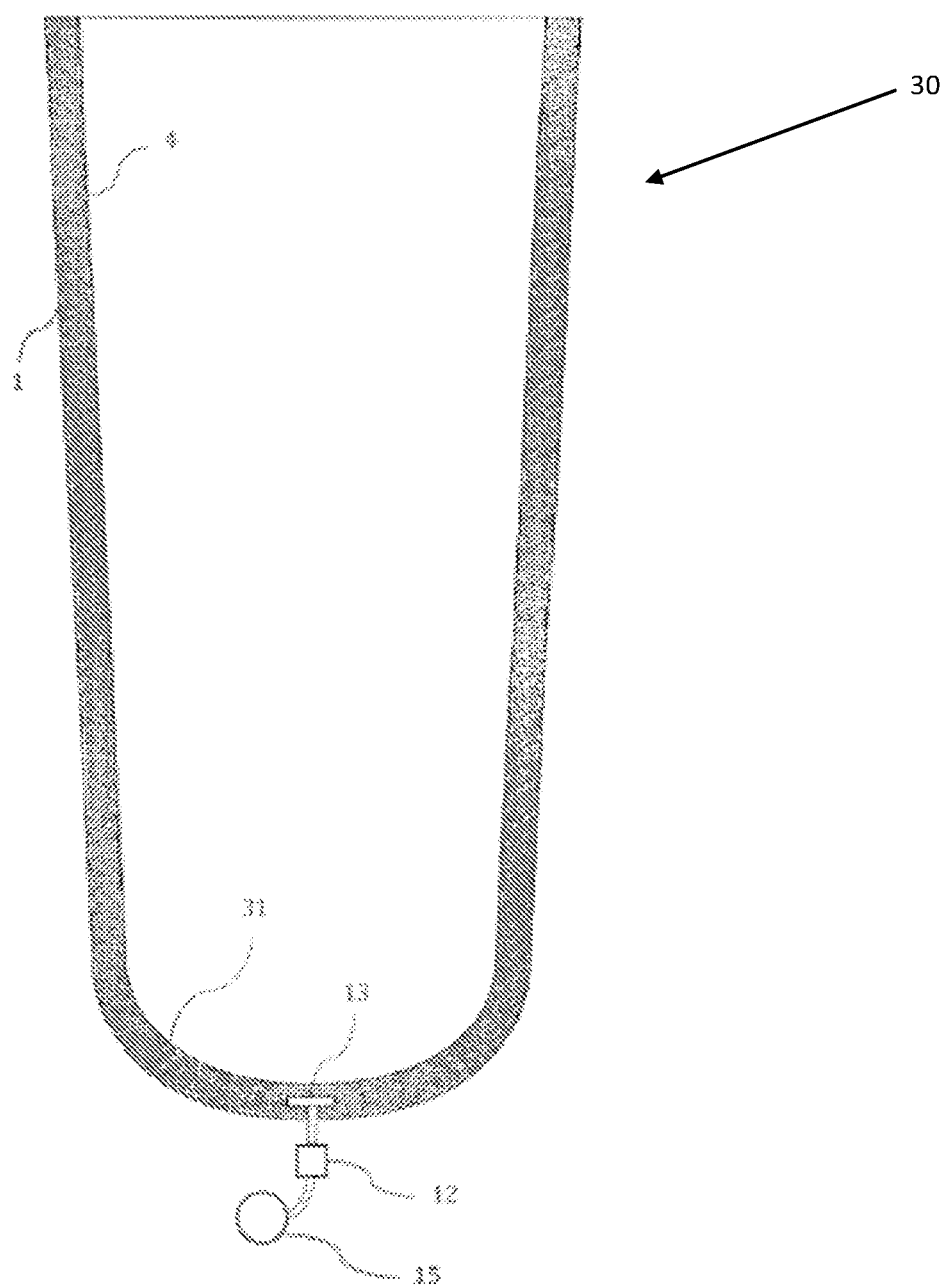
FIG. 11 shows a cross-sectional view of another lining arranged as a tube in accordance with an embodiment.

FIG. 11 depicts a cross-sectional view of yet another embodiment of a tubular lining 30. In the depicted embodiment, the lining 30 includes a closed end 31 in which a vacuum port is disposed; however it is noted that the vacuum port may be located at any suitable location on the liner, as the disclosure is not so limited.

As described above, a lining as described herein may be particularly advantageous in various applications related to prosthetic and orthotic applications. In particular, the lining may provide the potential to produce a variety different types of prosthetics and orthotics which may conform to a myriad of unique geometries and shapes so as to create a custom contoured support device. Such a device can be made increasingly rigid or compliant in a simple, convenient manner, providing for a custom fit device without need for traditional molding and fitting processes. It can be appreciated that the degree of rigidity of the lining may be adjusted, as desired, for example, depending on the strength of the vacuum applied. Furthermore, a lining according to the present disclosure may enable a class of prosthetics which may be repeatedly adjusted during use to maintain a comfortable and supportive fit.

In use, a lining while in the flexible state, may be placed around a body part, such as a residual limb or other part of the body to which a device is attachable, and from which a desired contour will be molded to create the desired shape and volume. Once in place, a partial vacuum of a suitable degree may be applied to the internal volume of the lining, causing the conformable material to transition from a compliant (non-jammed) state to a more rigid (jammed) state, thus increasing the hardness of the lining. The impermeable outer layer(s) of the lining may be molded to a residual limb in such a manner as to hold the appendage securely and aid in distributing forces between weight-bearing and non-weight-bearing portions of the residual limb.

Repeating the process of increasing and decreasing the vacuum and tailoring the rigidity and compliance of the lining may allow for additional alignment and fine-fitting of a prosthetic device. For example, a user may put weight on a prosthetic device and partially release the vacuum to allow for a limited amount of deformation of the conformable material, and then reapply the vacuum to more completely harden the conformable material into more desirable fit. Furthermore, at a later time when the shape of the body part may have naturally changed in contour and/or volume, the lining may be further adjusted by first reducing the vacuum and allowing fluid/gas to be supplied or otherwise enter into the internal volume, which allows for the conformable material to be adjusted and fit to the altered shape, and then subsequently aspirating the fluid/gas from the internal volume, causing the conformable material to harden into the adjusted shape.

Figure 12:
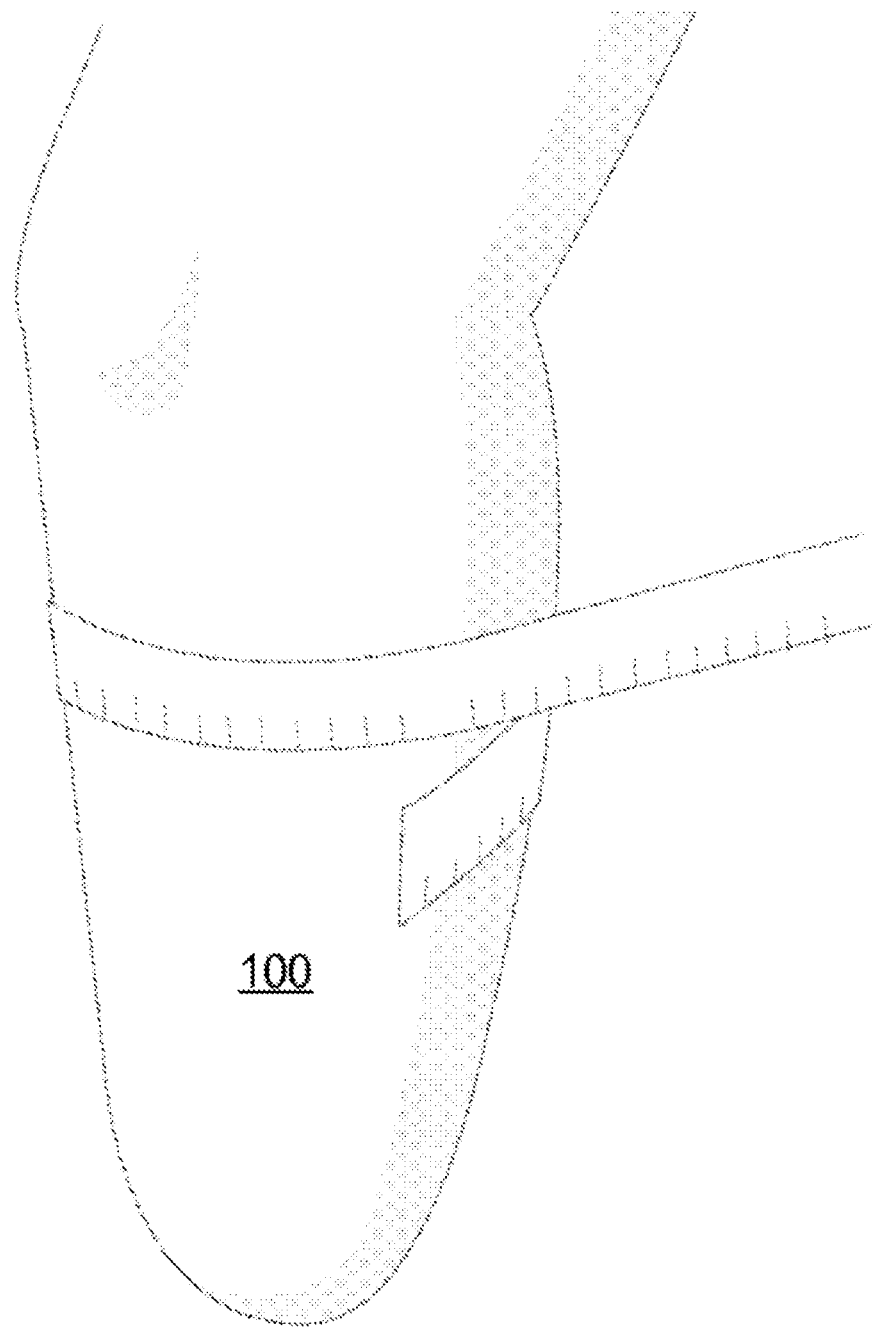
FIG. 12 illustrates a perspective view of a residual limb being measured in accordance with an embodiment.

FIGS. 12-22 depict an example of a process of fitting and use of a leg prosthesis incorporating a lining according to the present disclosure. In such applications, a lining is used in cooperation with a rigid socket which is custom shaped to a wearer's residual limb, as will be described in more detail below. It can be appreciated that any suitable process of fitting and use of a prosthesis, or any other appropriate apparatus, that can be fitted to the body may be employed, as the present disclosure is not so limited. FIG. 12 shows a schematic of a residual limb 100; the limb is measured to allow selection of an appropriately sized lining.

Figure 13:
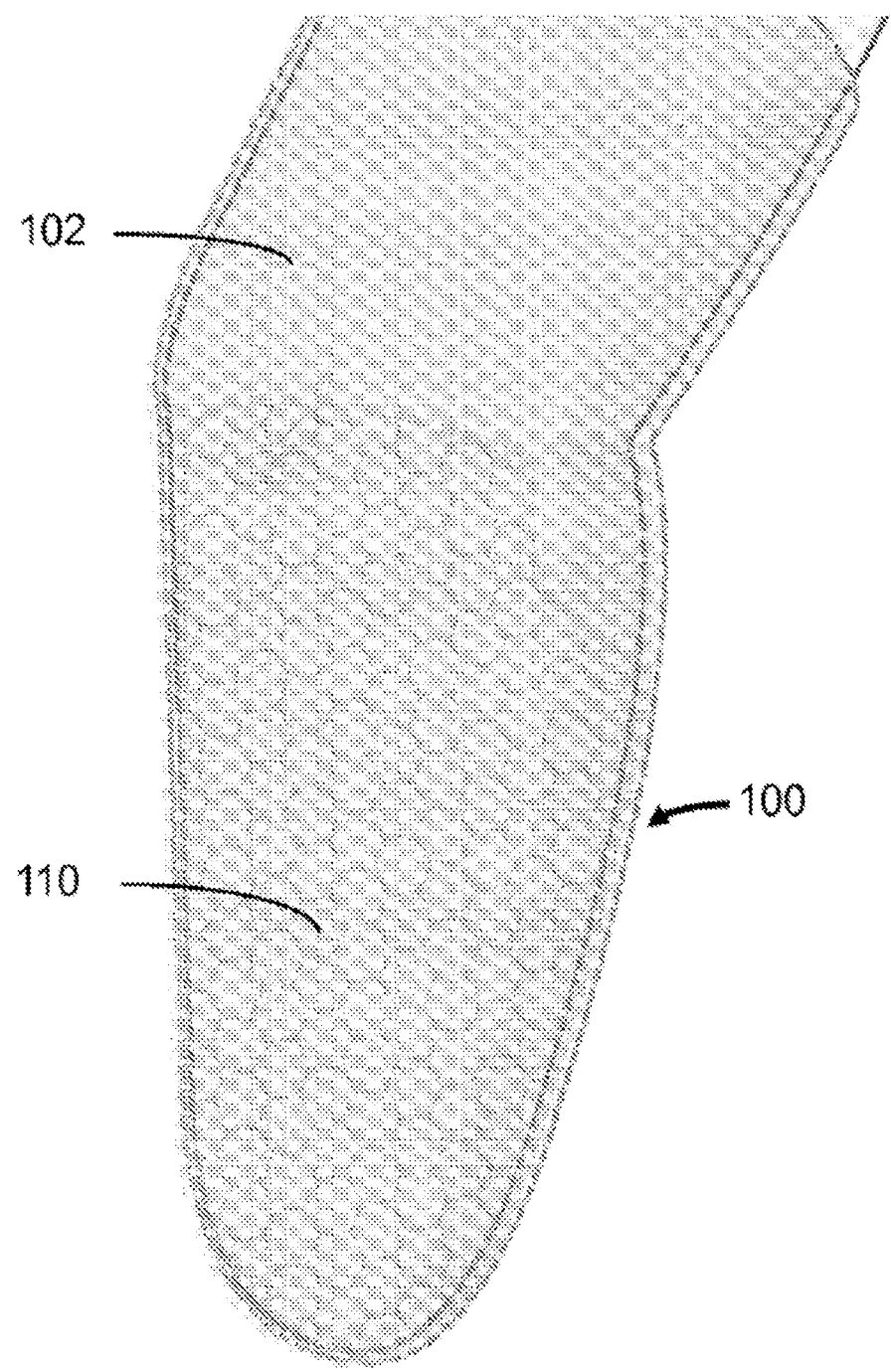
FIG. 13 depicts a perspective view of a residual limb fitted with a lining in accordance with an embodiment.

As shown in FIG. 13, a lining 102 is placed on with pressure applied to conform the lining to the shape of the residual limb 100. As discussed herein, the lining includes a number of barriers forming a plurality of compartments 110 each containing a conformable material therein. In the depicted embodiment, the compartments 100 feature a generally hexagonal shape. However, other patterns such as those described above may be used (e.g., employing a variety of shapes, densities, sizes, etc.), as the disclosure is not so limited.

Figure 14:
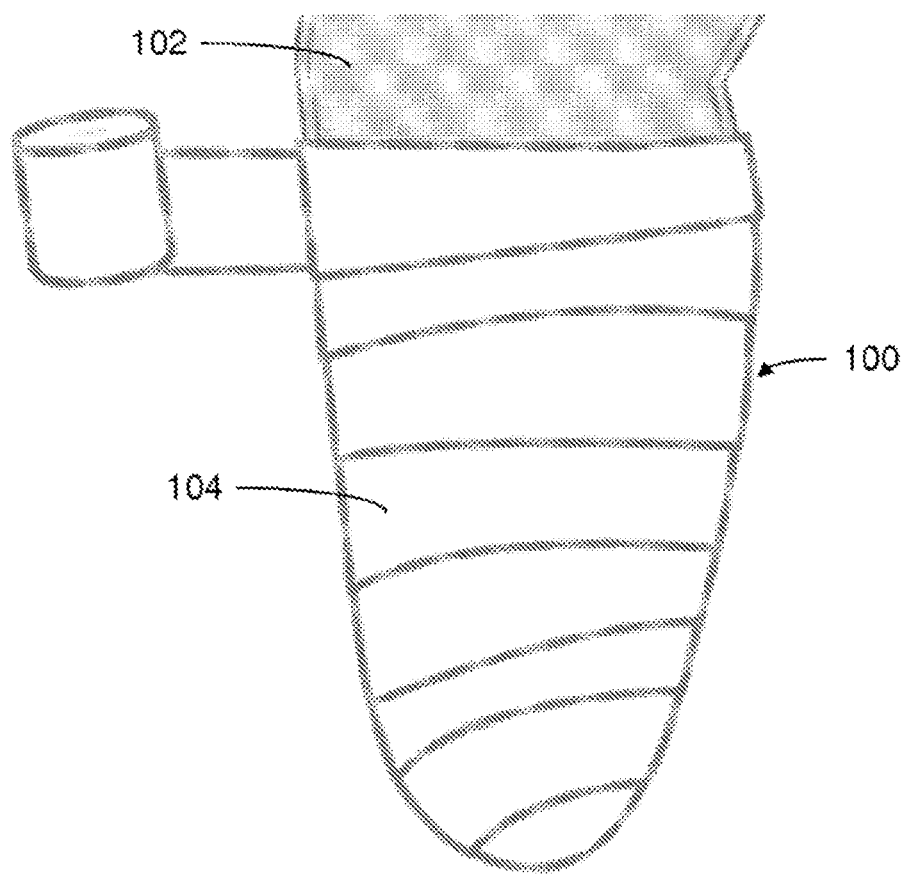
FIG. 14 shows a perspective view of a tape placed around the lining of FIG. 13.
Figure 15:
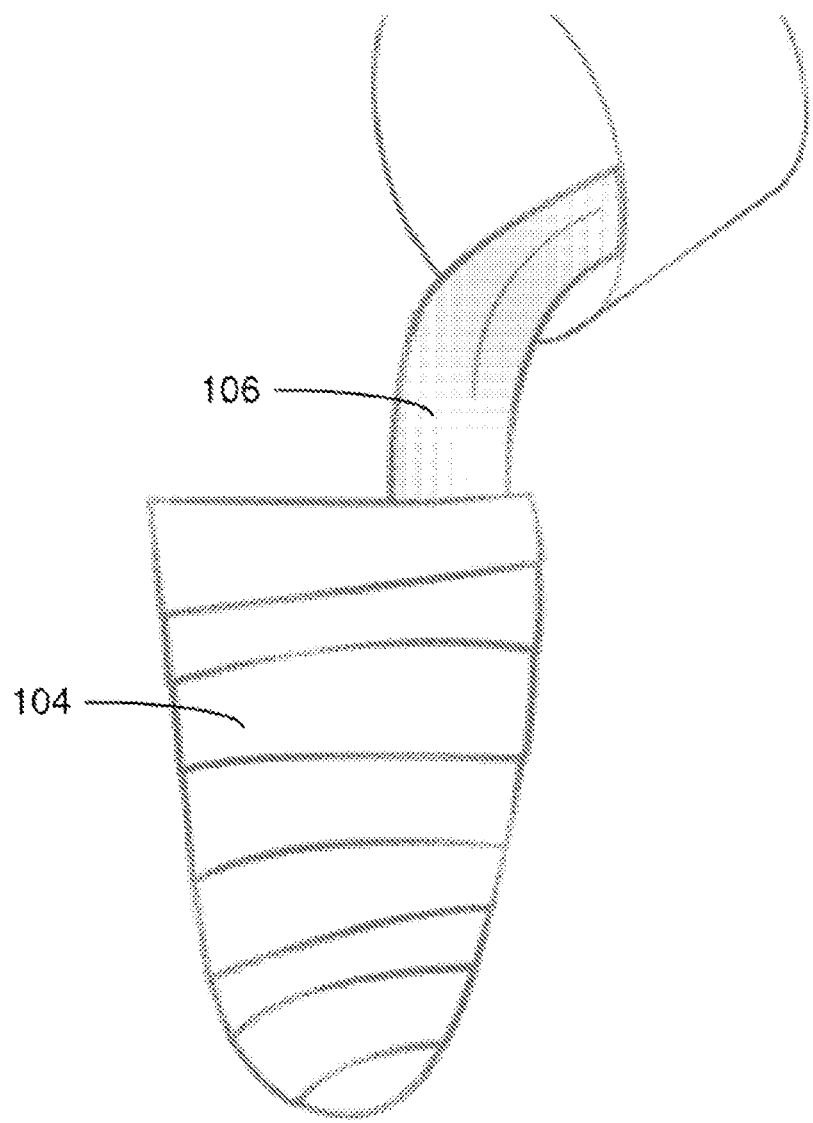
FIG. 15 depicts a perspective view of a mold cast using the tape of FIG. 14.
Figure 16:
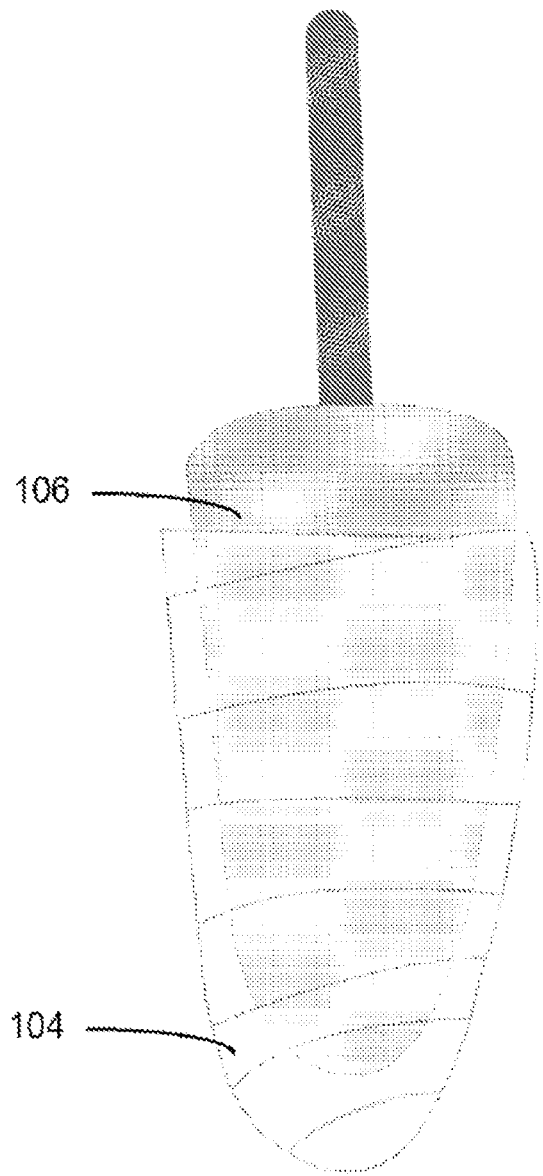
FIG. 16 illustrates a perspective view of the mold removed from the tape of FIGS. 14-15.
Figure 17:
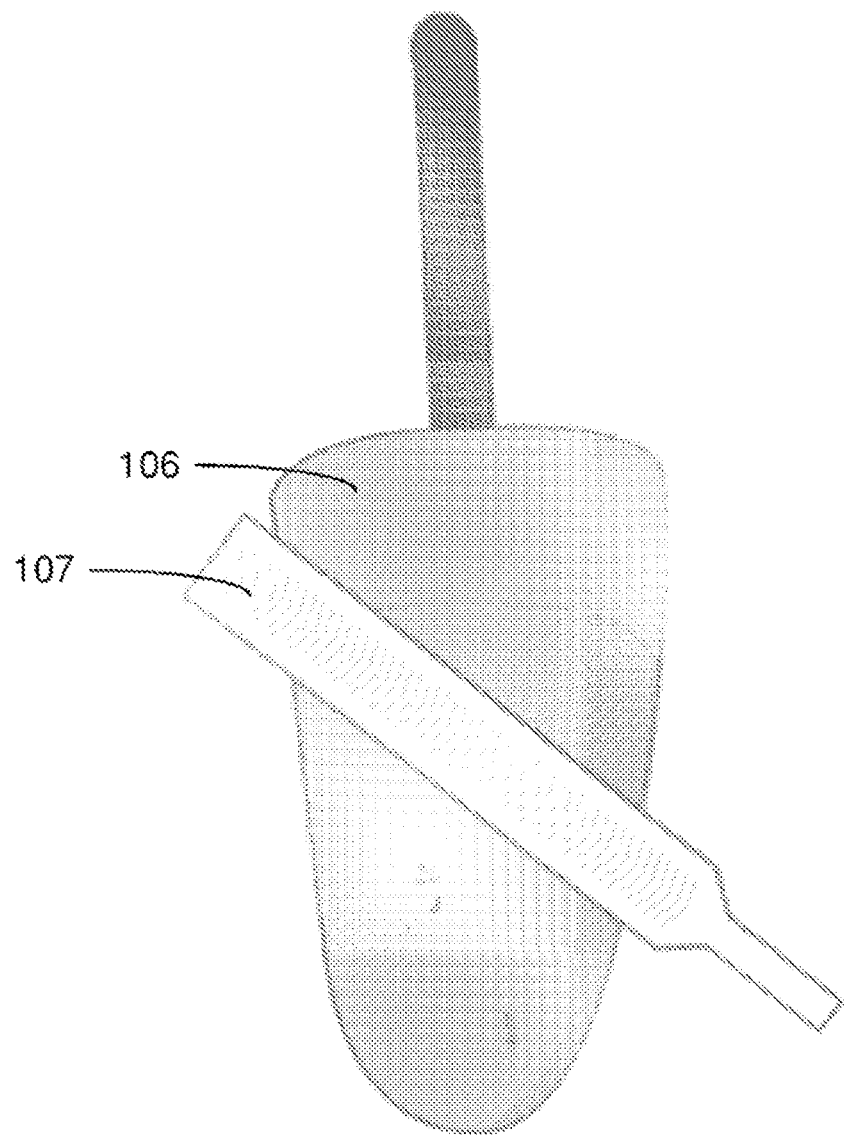
FIG. 17 shows a perspective view of the process of finishing the mold of FIG. 16.

Next, as depicted in FIG. 14, a gypsum tape cast 104 is made around the residual limb 100 and lining 102. The cast subsequently hardens into a negative mold and the residual limb and lining are removed. As shown in FIG. 15, a positive mold of the residual limb 100 is prepared by pouring plaster 106 into the hardened gypsum tape cast mold 104. As depicted in FIG. 16, the plaster 106 hardens into a plaster mold. And once hardened, as shown in FIG. 17, the plaster mold is finished by a prosthetist by shaping the mold with a suitable shaping tool 107, reducing the volume in areas which may correspond to soft tissues or to increase the volume corresponding to bony prominences.

Figure 18:
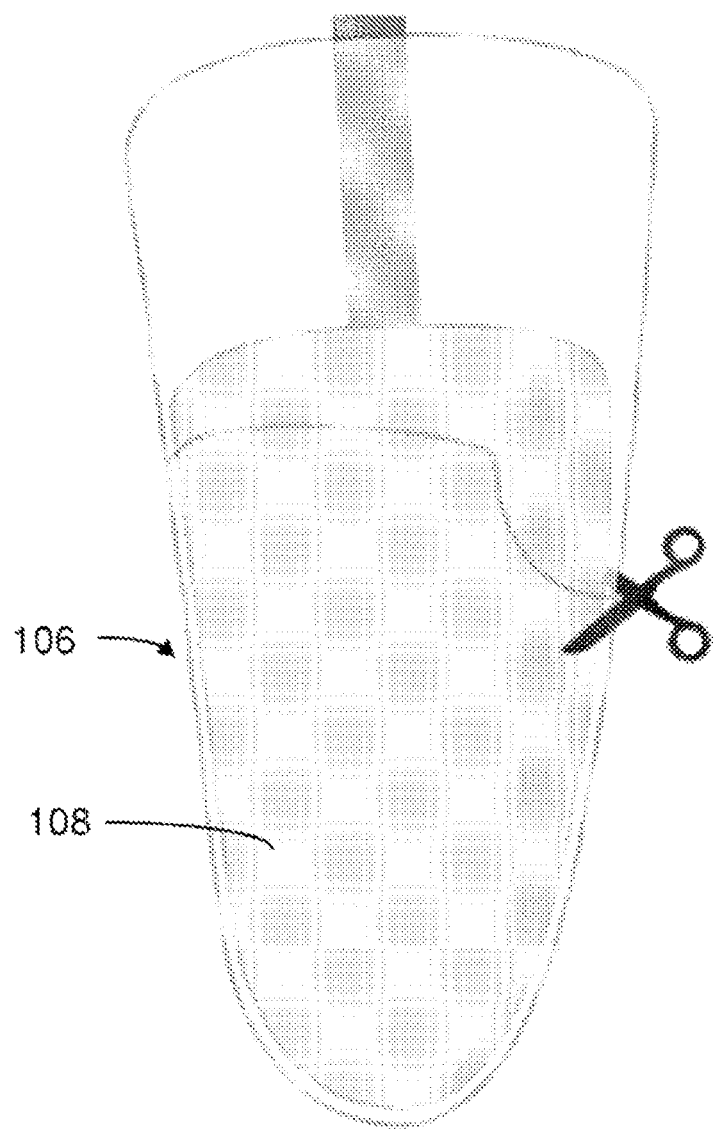
FIG. 18 depicts a perspective view of a layer placed over the mold of FIG. 17.
Figure 19:
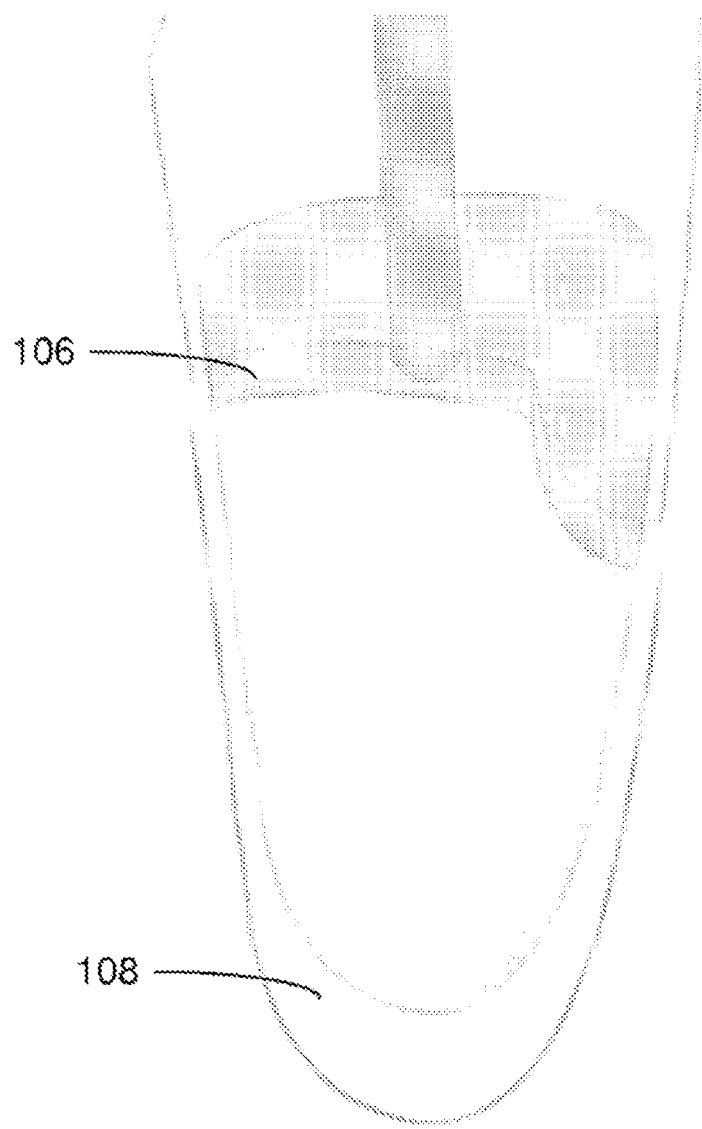
FIG. 19 shows a perspective view of the layer of FIG. 18 being formed.

Next, as shown in FIG. 18 a socket material 108 is vacuum formed over the finished plaster mold 106, and any excess material is removed. The mold 106 is subsequently removed from the finished socket material as depicted in FIG. 19. The socket material 108 may be made from any suitable material, for example, hard thermoset plastics.

Figure 20:
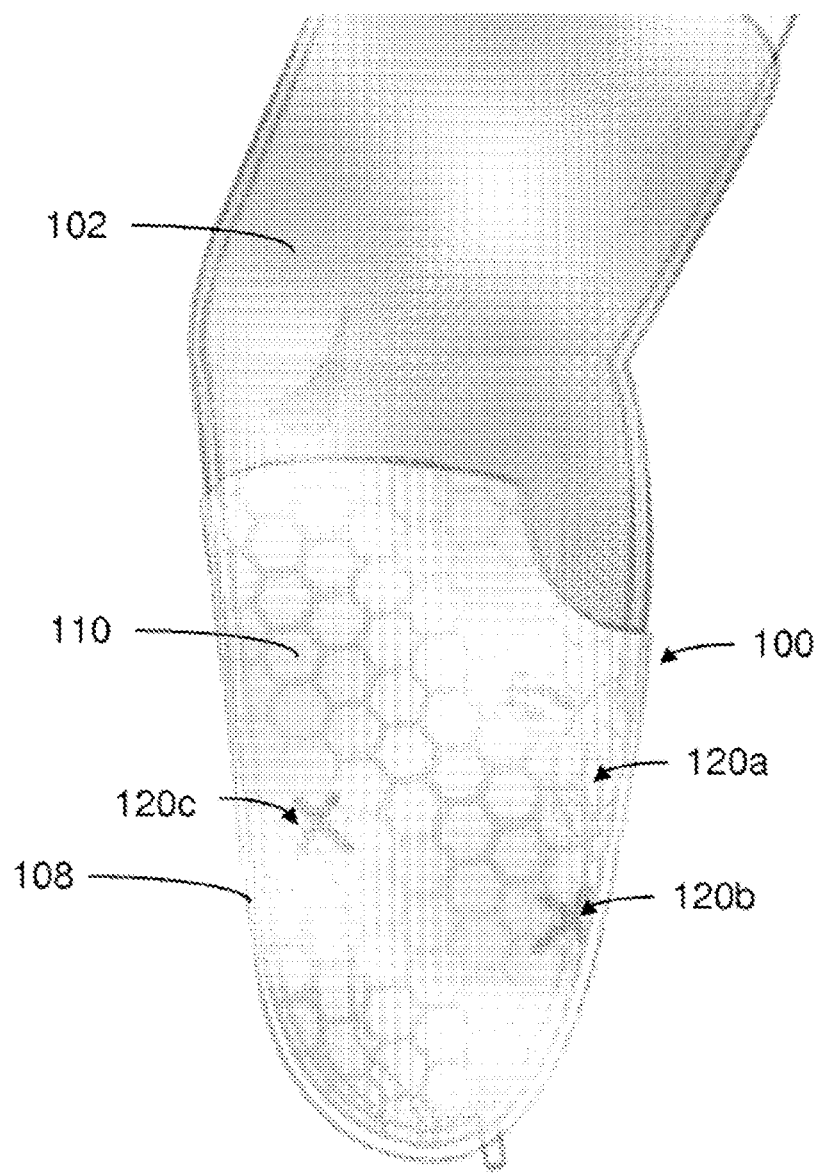
FIG. 20 illustrates a perspective view of the layer of FIG. 19 placed over the lining in accordance with an embodiment.

FIG. 20 depicts an initial fitting in which a user inserts the residual limb 100 and lining 102 into the socket material 108, and places weight on the socket-lining interface in order to identify areas of discomfort 120*a*, 120*b*, 120*c*. While not expressly shown in this figure, as discussed herein, the compartments of the lining may be patterned so as to align specific regions of the body with corresponding patterned regions of the lining. In some cases, certain patterned regions of the lining may be particularly suited to distribute pressure in a manner that results in a more comfortable, natural fit for the wearer. For example, the lining may be patterned so as to have a greater density of compartments corresponding to a region of the body part that typically experiences a higher level of mechanical stress (e.g., compression, torsion, other physical pressures, etc.) than other parts of the body. It can be appreciated that a greater density of compartments may also be suitable for regions of the body that do not commonly experience a relatively high level of mechanical pressure.

Figure 21:
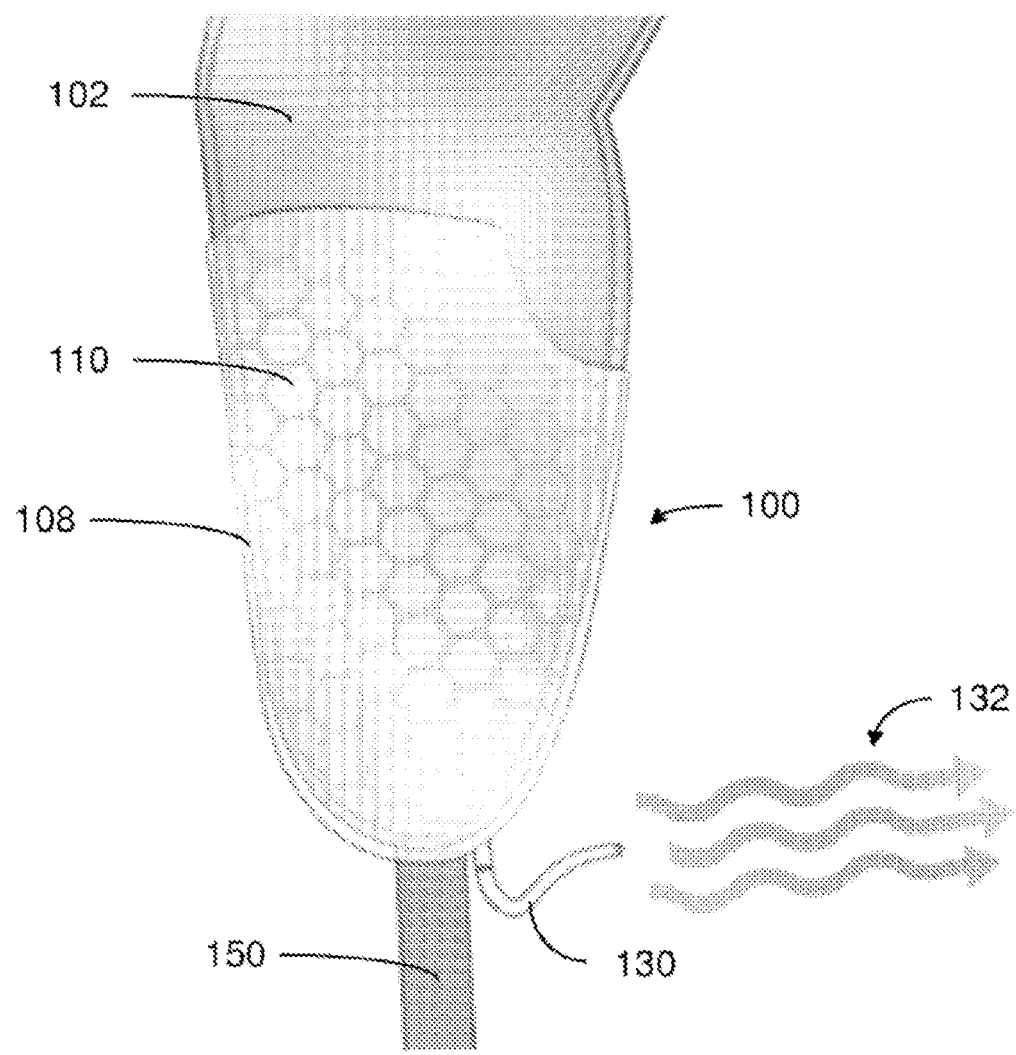
FIG. 21 shows a perspective view of the lining of FIG. 20 being aspirated in accordance with an embodiment.
Figure 22:
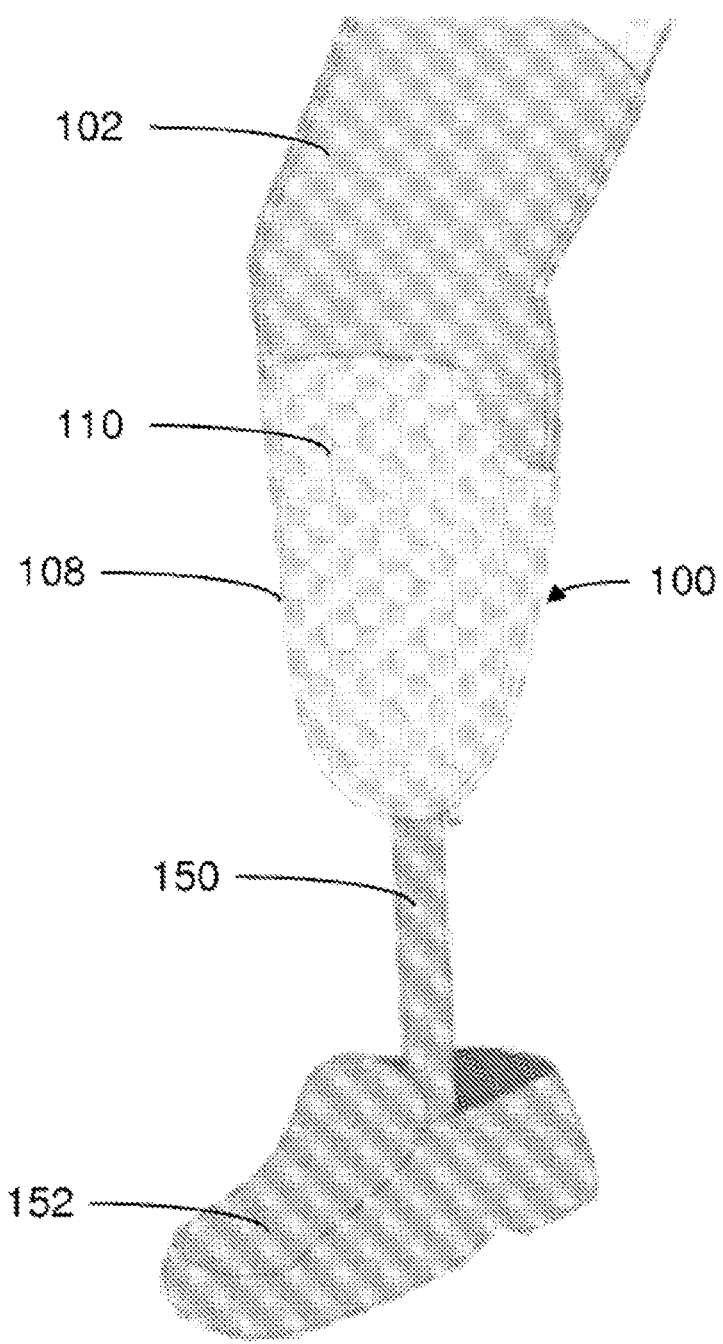
FIG. 22 depicts a perspective view of a prosthetic device attached to a body part in accordance with an embodiment.

As shown in FIG. 21, the pressure within the lining 110 is changed by applying vacuum to remove gas (e.g. air) 132 via an interface 130, or alternatively releasing a vacuum to allow gas to enter the lining 110. This allows the conformable material within the lining 110 to transition between compliant and rigid states and, in turn, allows the lining to adjust in shape such that the determined areas of discomfort 120*a*, 120*b*, 120*c* may be at least partially alleviated. As described above, as the residual limb may change shape over time, due to, for example, short term effects such as water retention or a user's activity level, long term effects such as weight loss, or other factors. Accordingly, the vacuum pressure within the lining 110 may be adjusted further to allow for adjustment of the fit and/or rigidity, as needed. FIG. 22 depicts a leg prosthesis further comprising a shaft 150 connected to a shoe 152.

Figure 7:
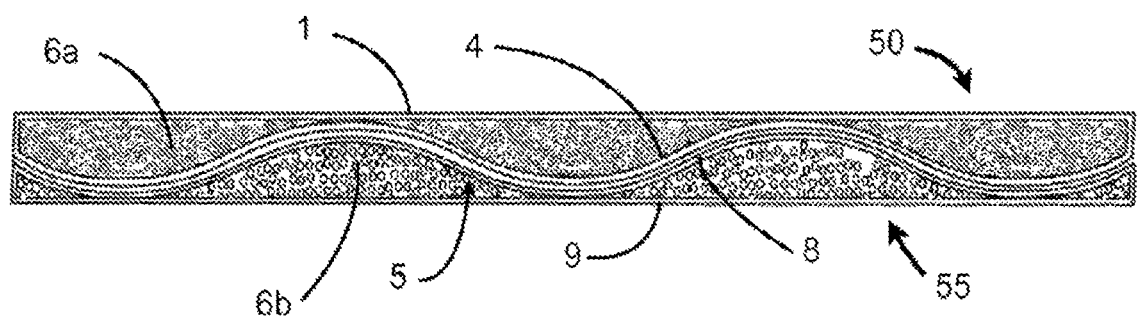
FIG. 7 depicts a cross-sectional view of multiple linings in accordance with an embodiment.

Referring back to the embodiment depicted in FIG. 7, the lining may be produced so as to allow for a two-stage fitting process of a wearable device, or other object. For example, such an embodiment may allow for an initial transition of the second layer 55 formed between a flexible impermeable outer portion 9 and a flexible impermeable intermediate portion 8 to become more rigid, so that a wearer may achieve an initial coarse fit. This initial fit may in turn provide for sufficient initial support so that more accurate alignment can be performed.

As shown in the depicted embodiment, the second layer 55 may include conformable material including larger particles 6*b* which may provide a stronger but less precise fit than the smaller particles 6*a* contained in the first layer 50 formed between a flexible impermeable outer portion 1 and a flexible impermeable intermediate portion 4. In the final stages of the fitting, in particular for achieving comfort, the second layer 55 may become more rigid to match and mechanically support the specific contours of a residual limb. In some embodiments, the second layer 55 may be configured to remain under a user's control for subsequent adjustment while the outer layer may be controlled (and sealed off) by a patient care provider (e.g., prosthetist).

An additional function of the lining disclosed herein may be to act as a suspension system in a prosthetic device, or other wearable apparatus. Such suspension systems of a lining may incorporate sheets of varying height and/or interlocking components which allow for a custom made socket to attach to a body part or lining to achieve a more secure fit. In one embodiment, a lining may further include a conformable material arranged with protrusions, or areas having varying height, of the lining which may provide for a mechanical coupling between the lining and a socket. Such protrusions may be designed to match relief sections arranged in a socket and thus form a mechanical interface. Accordingly, during donning of a prosthesis, the conformable material may provide a suitable level of compliance where the protrusions may be flexible so as to be able to be compressed into relief regions of the socket. Once vacuum is applied to the lining, the protrusions may become more rigid to prevent the lining from being released from the socket.

Embodiments of linings described herein may also be used for wound care applications. In some embodiments, a lining may be used in immediate post-operative prosthetic applications. For example, a lining may be included as part of a device to provide a support structure that can be constantly reconfigured to fit a limb which may be in a rapid state of change after an amputation. Furthermore, a lining may be integrated into a post-operative solution to provide a method of holding the shape of a compression dressing, or alternatively holding a residual limb in a compressed state.

Various orthotic applications utilizing the lining disclosed herein are also contemplated. For example, a lining containing conformable material may be included as a component of a splint or brace, or in a custom orthotic configured for foot, lumbar, wrist, ankle, knee, or shoulder support applications. In use, a lining for an orthotic device may be pressed onto a wearer and a subsequent vacuum may be applied to the lining to cause the conformable material to become more rigid and match the device to the wearer's unique physical geometry.

Additional compartments containing conformable material may be used to adjust the rigid structure for optimal fit and support. As described above, the lining may be repeatedly transitioned between the compliant and rigid states to allow readjustment such that a preferred shape or fit may be achieved. Furthermore, in some instances, a partial vacuum may be applied to a lining such that the lining achieves a state of intermediate rigidity. In such a state, fine tuning of the shape and/or thickness of portions the lining may be performed before applying a full vacuum to transform the lining into the fully rigid state and maintain a desired geometry.

In some embodiments, a lining may also have sensing capabilities. For example, in one embodiment, a lining may contain conductive material sandwiched within or impregnated into the outer impermeable layers. In such an embodiment, the lining may be configured to detect the distance between conductive layers via a change in capacitance or resistance. This may help to identify high pressure areas in a support device and sense the tolerances between a residual limb and a socket. In another embodiment, additional sensing capabilities may be provided by integrating a sensor within the conformable material. For example the sensing material may be able to be excited and then measured when the conformable material is in both the compliant and rigid states. Measurements of orientation, volume distribution, or stress of the conformable material may then be made to determine a distribution of forces and stresses throughout a device.

A lining according to the present disclosure may find additional uses in other applications requiring fitting to a part of a human body. Examples of such applications may include boots for skiing, skating and snowboarding, as well as helmets, seating and other impact protection gear. In some embodiments, as discussed above, linings described herein may be suitable for wound care devices and applications thereof.

Furthermore, applications for a lining outside of the context of fitting to a body part are also contemplated. A lining may be used in myriad applications requiring fitting of a complex shape to a solid object, including as a packaging insert for shipping of complex shaped objects and expensive works of art such as sculptures and vases. The ability to cause the package to become increasingly rigid by applying vacuum to the liner and then later release the vacuum to allow unpacking and reuse of a packaging insert of this type.

Alternatively, the lining may be used for applications in packaging of non-perishables or perishables (e.g., food, produce, etc.).

Having thus described several aspects of at least one embodiment of this invention, it is to be appreciated various alterations, modifications, and improvements will readily occur to those skilled in the art. For example, the devices described herein may be adapted for use in medical or non-medically related applications. Such alterations, modification, and improvements are intended to be part of this disclosure, and are intended to be within the spirit and scope of the invention. Accordingly, the foregoing description and drawings are by way of example only.

What is claimed is:

1. A lining for providing custom contoured fitting between a rigid prosthetic/orthotic device and a corresponding residual limb, comprising:
    a flexible sheet including a fluid impermeable outer portion enclosing an internal volume;
    a plurality of barriers forming a plurality of compartments secured in place within the internal volume, at least one of said compartments having a wall formed by one of said barriers, wherein a length of the barrier forming said wall is more than 2 times greater than a distance traversed by said barrier along said compartment, whereby said wall comprising a corrugated barrier structure; and
    a conformable material located within at least some of the plurality of compartments, the plurality of barriers being permeable to gas and impermeable to the conformable material,
    whereby said lining is configured to provide custom contoured support of said residual limb in contact with said rigid prosthetic/orthotic device.

2. The lining of claim 1, wherein the flexible sheet includes at least one of an elastomer, silicone, polyurethane, rubber, woven material and an elastic polymeric material.

3. The lining of claim 1, wherein at least one of the plurality of barriers includes at least one of a flexible material, elastic material, woven material, porous material, breathable material, sponge, foam, cork and knit.

4. The lining of claim 1, wherein at least one of the plurality of barriers is permeable to liquid.

5. The lining of claim 1, wherein at least one of the plurality of barriers extends transversely across from a first portion of the flexible sheet to a second portion of the flexible sheet, the first and second portions of the flexible sheet located on opposing sides of the internal volume.

6. The lining of claim 1, wherein at least one of the plurality of barriers is attached to the flexible sheet.

7. The lining of claim 1, wherein at least one of the plurality of barriers has an average pore size of less than 1.0 mm.

8. The lining of claim 1, wherein at least one of the plurality of barriers is constructed and arranged to elongate or contract during bending of the flexible sheet.

9. The lining of claim 1, wherein at least one of the plurality of barriers includes at least one of a biasing element within said corrugated structure.

10. The lining of claim 1, wherein an average thickness of the plurality of barriers is between 0.01 mm and 10.0 mm.

11. The lining of claim 1, wherein the flexible sheet includes a first fluid impermeable flexible layer and a second fluid impermeable flexible layer, coupled to one another to form a seal between the internal volume and an external environment.

12. The lining of claim 1, wherein the conformable material includes a granular material including a plurality of particles.

13. The lining of claim 12, wherein the plurality of particles are configured to interlock with one another.

14. A method of installing a lining for fitting a rigid prosthetic/orthotic device to a corresponding residual limb, comprising placing the lining over the residual limb such that an inner surface of the lining conforms to a shape of the residual limb external body part, the lining including a flexible sheet having a fluid impermeable outer portion enclosing an internal volume, a plurality of barriers forming a plurality of compartments within the internal volume, at least one of said compartments having a wall formed by one of said barriers, wherein a length of the barrier forming said wall is more than 2 times greater than a distance traversed by said barrier along said compartment, whereby said wall comprising a corrugated barrier structure, and a conformable material located within at least some of the plurality of compartments; and aspirating fluid from the plurality of compartments within the internal volume, wherein the aspiration of fluid limits both deformation of the conformable material and shape adjustment of the flexible sheet.

15. The method of claim 14, further comprising supplying fluid to the plurality of compartments within the internal volume, permitting deformation of the conformable material and shape adjustment of the flexible sheet.

* * * * *